US010294518B2

(12) United States Patent
Kamps-Hughes et al.

(10) Patent No.: US 10,294,518 B2
(45) Date of Patent: May 21, 2019

(54) METHODS AND SYSTEMS FOR ULTRA-SENSITIVE DETECTION OF GENOMIC ALTERATIONS

(71) Applicant: Fluxion Biosciences, Inc., South San Francisco, CA (US)

(72) Inventors: Nicholas Kamps-Hughes, Oakland, CA (US); Cristian Ionescu-Zanetti, Berkeley, CA (US)

(73) Assignee: Fluxion Biosciences, Inc., Alameda, CA (US)

( * ) Notice: Subject to any disclaimer, the term of this patent is extended or adjusted under 35 U.S.C. 154(b) by 159 days.

(21) Appl. No.: 15/268,349

(22) Filed: Sep. 16, 2016

(65) Prior Publication Data

US 2018/0080068 A1    Mar. 22, 2018

(51) Int. Cl.
G06F 19/22 (2011.01)
C12Q 1/6827 (2018.01)

(52) U.S. Cl.
CPC ........... *C12Q 1/6827* (2013.01); *G06F 19/22* (2013.01)

(58) Field of Classification Search
None
See application file for complete search history.

(56) References Cited

U.S. PATENT DOCUMENTS

| 7,822,556 | B2 | 10/2010 | Akilesh et al. |
| 9,050,280 | B2 | 6/2015 | Vlassenbroeck et al. |
| 2012/0220478 | A1 | 8/2012 | Shaffer |
| 2014/0066317 | A1 | 3/2014 | Talasaz |

FOREIGN PATENT DOCUMENTS

| WO | 2007-089583 A2 | 8/2007 |
| WO | 2011-011426 A2 | 1/2011 |
| WO | 2016-009224 A1 | 1/2016 |

OTHER PUBLICATIONS

Anders, Simon et al., "Differential expression analysis for sequence count data", Genome Biology, Oct. 27, 2010, R106, 12 pgs.
Applied Biosystems, "TaqMan Mutation Detection Assay—Competitive Allele-Specific TaqMan PCR", Life Technologies, Apr. 2012 (Pub No. 4467011 Rev. B), 51 pgs.
Auer, Paul L. et al., "Statistical Issues in Next-Generation Sequencing", 21st Annual Conference Proceedings, Annual Conference on Applied Statistics in Agriculture, Paper #6, Kansas State University, Apr. 19, 2009, 16 pgs.
Beltman, Joost B., et al., "Reproducibility of Illumina platform deep sequencing errors allows accurate determination of DNA barcodes in cells", BMC Bioinformatics, Apr. 2, 2016, 16 pgs.
Cameron, Colin A., et al., "Essentials of Count Data Regression", Univeristy of California at Davis (UC Davis), Jun. 30, 1999, 17 pgs.
Cameron, Colin A., et al., "Regression Analysis of Count Data", Second Edition, Cambridge University Press, May 27, 2013, 27 pgs.
Cherukuri, Praveen F., et al., "Replicate exome-sequencing in a multiple-generation family: improved interpretation of next-generation sequencing data", BMC Genomics, Nov. 25, 2015, 10 pgs.
Cui, Xiangqin et al., "Statistical tests for differential expression in cDNA microarray experiments", Genome Biology, vol. 4, Issue 4, Article 210, Mar. 17, 2003, 10 pgs.
Exiqon, "A guide to the whole transcriptome and mRNA Sequencing Service", While Transcriptome and mRNA NGS Services, Guidelines v1.2, Oct. 2014, 20 pgs.
Flaherty, Patrick et al., "Ultrasensitive detection of rare mutations using next-generation targeted resequencing", Nucleic Acids Research, vol. 40, No. 1, Oct. 11, 2012, 12 pgs.
Frampton, Garrett M., et al., "Development and validation of a clinical cancer genomic profiling test based on massively parallel DNA sequencing", Nature Biotechnology, vol. 31, No. 1, Oct. 20, 2013, pp. 1023-1033.
Genohub, "Designing your Next Generation Sequencing Run", Guide to Next-Gen Sequencing, Jun. 14, 2016, 6 pgs.
Hiatt, Joseph B., et al., "Single molecule molecular inversion probes for targeted, high-accuracy detection of low-frequency variation", Genome Research, Cold Spring Harbor Laboratory Press, Feb. 2, 2013, pp. 843-854.
Lanman, Richard B., et al., "Analytical and Clinical Validation of a Digital Sequencing Panel for Quantitative, Highly Accurate Evaluation of Cell-Free Circulating Tumor DNA", PLoS One, vol. 10, No. 10, Oct. 16, 2015, 27 pgs.
Liu, Yuwen, et al., "RNA-seq differential expression studies: more sequence or more replication?" Bioinformatics, vol. 30, No. 3, Dec. 6, 2014, pp. 301-304.
Manion, Megan et al., "Deep Sequencing Analysis and Low Frequency SNP/Mutation Detection with NextGENe Software", NextGENe by SoftGenetics, SoftGenetics LLC Whitepaper, Apr. 1, 2009, 4 pgs.
McElroy, Kerensa et al., "Accurate single nucleotide variant detection in viral populations by combining probabilistic flustering with a statistical test of strand bias", BMC Genomics, vol. 14, Jul. 24, 2013, 12 pgs.
Newman, Aaron M., et al., "An ultrasensitive method for quantitating circulating tumor DNA with broad patient coverage", Nature Medicine, Nature America Inc., Apr. 6, 2014, 9 pgs.
Peng, QUan et al., "Reducing amplification artifacts in high multiplex amplicon sequencing by using molecular barcodes", BMC Genomics, vol. 16, Aug. 7, 2015, 12 pgs.
Robasky, Kimberly et al., "The role of replicates for error mitigation in next-generationi sequencing", Nature—Reviews—Genetics, Perspectives, vol. 15, Jan. 2014, pp. 56-62.

(Continued)

*Primary Examiner* — John S Brusca
(74) *Attorney, Agent, or Firm* — Asif Ghias

(57) ABSTRACT

The invention discloses methods and apparatuses for the detection and diagnostics of genetic alterations/mutations in a target sample, which may be a solid tissue or a bodily fluid. A reference sample is also acquired, and the target and reference samples are replicated into multiple target and reference replicates. The replicates are sequenced, and the sequence data is analyzed based on a statistical test. The statistical test compares the measurements between the target and reference replicates at respective allelic indices. True positive calls are then made based on the results of the statistical testing, and the desired genetic alterations/mutations are identified at the base-pair level. The invention may be used for diagnostics related to cancer, auto-immune disease, organ transplant rejection, genetic fetal abnormalities and pathogens.

19 Claims, 6 Drawing Sheets

(56) References Cited

OTHER PUBLICATIONS

Robin, Jerome D., et al., "Comparison of DNA Quantification Methods for Next Generation Sequencing", Nature—Scientific Reports, Apr. 6, 2016, pp. 1-10.
Schmitt, Michael W., "Detection of ultra-rare mutations by next-generation sequencing", Proceedings of the National Academy of Sciences (PNAS), vol. 109, No. 36., Sep. 4, 2012, pp. 14508-14513.
Spencer, David H., et al., "Performance of Common Analysis Methods for Detecting Low-Frequency Single Nucleotide Variants in Targeted Next-Generation Sequence Data", The Jouirnal of Molecular Diagnostics, vol. 16, No. 1, Jan. 16, 2014, pp. 75-88.
USDHHS, U.S. Department of Health and Human Services—FDA, "Guidance for Industry—Bioanalytical Method Validation", Draft Guidance Rev. 1, Biopharmaceutics, Sep. 2015, 34 pgs.
Williams, Chris, "New Method for Identifying Genetic Alterations that Modulate Gene Expression", Columbia University Medical Center, Columbia University Department of Systems Biology, Mar. 25, 2016, 3 pgs.
Zhang, Yanfeng et al., "Improved Variant Calling Accuracy by Merging Replicates in Whole-Exome Sequencing Studies", Research Article, BioMed Research International, Hindawi Publishing Corporation, Aug. 4, 2014, pp. 1-8.
Zhang, Yanfeng et al., "Mutation Detection in an Antibody-Producing Chinese Hamster Ovary Cell Line by Targeted RNA Sequencing", Research Article, BioMed Research International, Hindawi Publishing Corporation, Feb. 21, 2016, pp. 1-8.
PCT-US2017-051489_InternationalSearchReportAndWrittenOpinion_ dated Dec. 22, 2017.

METHODS AND SYSTEMS FOR ULTRA-SENSITIVE DETECTION OF GENOMIC ALTERATIONS

FIELD OF THE INVENTION

This invention relates generally to the field of detection of genetic/genomic alterations or mutations. This invention is particularly related to the detection and diagnosis of genetic alterations using ultra-sensitive techniques capable of detecting mutant material at very low allele frequencies (AF).

BACKGROUND ART

Amplicon-based targeted sequencing

Next Generation Sequencing (NGS) has been an active area of focus for a large number of organizations. Commercial corporations and Research and Development (R&D) outfits perform NGS of tumor samples in order to determine the presence of genetic/genomic alterations in the DNA or RNA of patient samples. A key application of interest is the determination of somatic alterations in tumor biopsy samples from cancer patients.

Such alterations can be used to determine the tumor type and disease aggressiveness, and have been shown to be correlated to the patient's clinical response to different therapies. In some cases, the efficacy of existing therapies is directly linked to the presence of specific alterations such as Kirsten Rat Sarcoma (KRAS) and Epidermal Growth Factor Receptor (EGFR) mutations. In general, somatic mutation detection is effectively used by physicians for therapy selection, prognosis and diagnosis.

Targeted sequencing for somatic mutation detection refers to the selection of only certain portions of the genome that are to be sequenced. This is often achieved by over-amplifying certain portions of the genome, typically consisting of a finite number of contiguous sequences from 70 to 200 bases in length. These bases are termed amplicons. There may be hundreds to thousands of amplicons assembled as part of an amplicon panel that covers the genes important to a certain type of cancer.

The advantage of amplicon sequencing is the ability to sequence at a higher depth, for a lower price, by concentrating on regions of the genome where alterations are likely to occur. Organizations offering targeted sequencing based somatic mutation detection on a commercial scale include Foundation Medicine, and cancer center sequencing labs at outfits such as MD Anderson, Cleveland Clinic, and Stanford Cancer Center.

There are two important limitations to both targeted sequencing and other sequencing for the determination of somatic mutations/alterations:

(1) Insufficient Availability of Tissue

That is because this type of sequencing requires a tumor biopsy. Traditional biopsy procedures often have significant associated risks and loss of quality of life for the patient, and can only be performed a few times during the disease progression cycle. If a sample is compromised for any reason, it is often impossible to obtain a second tissue sample from the same patient. Furthermore, in some cases, due to the tumor's location in an inaccessible region, a traditional biopsy is not feasible.

(2) Low Tumor Content

While the introduction of Fine Needle Aspirate (FNA) procedures have reduced the risks and discomfort associated with biopsies, the resulting samples are much less abundant and contain a variable ratio of tumor-derived to normal tissue DNA. Most commercially available tests require at least 20% tumor to normal tissue content, as reported in the Non-Patent Literature (NPL) reference "Development and validation of a clinical cancer genomic profiling test based on massively parallel DNA sequencing", dated November, 2013 by Frampton et al., and appearing in Nature Biotechnology, Volume 31, Number 11.

The tumor purity requirement is dictated by the limits of standard sequencing and variant calling, which does not function well below 5% Allele/Allelic Frequency (AF). Making calls below 5% AF leads to a high number of false positive (FP) calls. Therefore, typical diagnostic pipelines only call mutants if they are above AF 5%. Some tests go down to 3% AF, but do not call below that level since significant numbers of FP calls would be made. These errors preclude the use of samples where tumor material is not sufficient, i.e. below the 20% tumor to normal tissue ratio.

Because of the above limitations, it is apparent that higher sensitivity and specificity sequencing will be beneficial to tumor biopsy profiling where the biopsies have low tumor content. That is one shortcoming of the prior art that the instant invention addresses. The instant approach leads to a higher percentage of measurable samples.

Liquid Biopsies and NGS

The limitations of solid tumor biopsies include its high cost, associated complications and inability to track tumor progression over time. To address these limitations, several non-invasive avenues of obtaining tumor-derived nucleic acids (RNA, DNA) have been proposed. Starting samples obtained from the patient include but are not limited to, blood or blood components, urine, stool samples, pleural fluid, ascites, or sputum. The chief advantage of a minimally invasive biopsy (or a liquid biopsy) is that samples are easily obtained at minimal risk to the patient.

The samples can also be obtained at many time points during diagnosis and treatment. If somatic variants can be accurately detected in such samples, it is possible to track the changes in tumor mutation burden over time, because the variants demonstrate correlation to mutations present in the primary tumor. Furthermore, such minimally invasive or non-invasive testing can even be used pre-diagnosis, as a screening tool for the general population.

A key challenge for liquid biopsies is the very low tumor content as compared to a tumor biopsy, ranging from <0.1% AF to about 10% AF in advanced patients. Liquid biopsy should be taken to include all liquid sample types, including cell free DNA (cfDNA) and circulating tumor cells (CTCs) that have a background of wild type DNA from either white blood cells or the rest of the plasma. In earlier stage patients or patients with certain cancer types, these fractions are even lower, from <0.01% AF to 0.5% AF. To address this challenge, a number of approaches have been put forward:

(A) Deep Sequencing: Increased Read-Depth

Increasing the depth of sequencing (or the number of sequence reads at a certain locus/location) provides the advantage of more accurately determining the percentage of mutant molecules present in the sample. This gives the ability to detect a greater number of reads derived from the mutated DNA. This in turn offers the possibility of detecting low AF variants. For example, a 0.1% AF variant requires 10,000 overall reads in order to have at least 10 reads of the mutant molecule compared to 9,990 of the wild type molecule reads.

Similarly, increasing depth even further may provide a more accurate representation of the true mutant percentage.

Despite these advantages, replication errors such as those produced in Polymerase Chain Reaction (PCR) and other errors that recur in the replication and/or sequencing processes, persist and cannot be eliminated by simply increasing the read-depth. The propensity of such errors may be reduced by using higher fidelity enzymes during the replication process. However, these errors can never be eliminated altogether and constitute a large background of falsely detected mutations at AFs below 0.5%.

(B) Reference Sample and Background Error Rate

One approach for reducing the false positive rate is the use of a reference sample. This is typically a sample extracted from the same patient, but one that does not include tumor material. This is helpful in that any alterations present in the reference sample can be assumed to be due to inherited difference of the patient genome from the reference genome i.e. germline mutations. If called during the somatic mutation testing, these can be eliminated as false positives (FP).

In cases where the matched normal is not available from the same clinical patient, a "normal" DNA control sample may be drawn from another matching donor with a healthy tissue or bodily fluid known to be devoid of somatic mutations. In this case, while the alterations in the reference sample are not due to inherited differences, they can still be eliminated as FPs because they belong to the donor who is known to be healthy. This can eliminate FPs in places where there are systematic errors. However, this process cannot eliminate errors due to the misdetection of germline mutations as somatic.

A benefit of this approach is that it can also detect abnormalities that are due to contamination if the contamination source happens to be the same for the reference and tumor samples. Similarly, this approach can also detect very high likelihood alterations due to replication and sequencing errors. The reader is again referred to NPL reference "Development and validation of a clinical cancer genomic profiling test based on massively parallel DNA sequencing", dated November, 2013 by Frampton et al., and appearing in Nature Biotechnology, Volume 31, Number 11, For a related approach based on estimating background error rate, the reader is referred to NPL references "Ultrasensitive detection of rare mutations using next-generation targeted resequencing", dated October 2011 by Flaherty et al., appearing in Nucleic Acids Research, Volume 40, and "Analytical and Clinical Validation of a Digital Sequencing Panel for Quantitative, Highly Accurate Evaluation of Cell-Free Circulating Tumor DNA" dated October 2015 by Lanman et al., appearing in Public Library of Science's PLOS ONE publication, Digital Object Identifier (DOI): 10.1371/journal.pone.0140712.

Specifically, in Flaherty et al., a single target sample sequence measurement is compared to the background distribution to generate a p-value using the beta-binomial distribution. The shortcoming of this approach, however, is that it requires very high read-depth (approx. 10E6 read-depth) and was only tested with 300 base-pairs (bp). Even at this very high read-depth, there is still generally a high FP rate, i.e. the described specificity of 0.99 at a detection floor of 0.1% AF means that there is still 1 FP per 100 bp at a reasonable sensitivity. This means that for a typical 40 kilo base-pair (kbp/kb) sized amplicon panel, one would still find a relatively high number of false positives i.e. about 400. Additionally, Lanman et al. also uses a high read-depth.

(C) Statistical Treatment of Sequencing Data

This set of approaches treat nucleic acid sequencing data with various statistical methods. For example, there are statistical tests for each sequence base read, typically reported as quality scores. These are then used for alignment quality scoring by either ruling in or ruling out each portion of the read.

In nucleic acid sequencing, replication of the target sample, or simply the target, assays has been used in gene expression studies. In such efforts, the quantity being measured is the copy number change for DNA or RNA molecules, which is typically related to the amount of gene expression i.e. over-expression or under-expression. For one example, see NPL reference "A guide to the whole transcriptome and mRNA Sequencing Service", dated October 2014 by Exiqon.

Similar suggestions can be found in NPL reference "Statistical Issues in Next-Generation Sequencing", dated 2009 by Auer et al. and appearing in the proceedings of the $21^{st}$ Annual Conference on Applied Statistics in Agriculture. This reference suggests the use of 4 sample replicates and two groups of samples, treated and untreated. It then uses Analysis of Variance (ANOVA) models to determine the true variance from noise, where the variance is determined as the change in the copy number for certain genes as compared to a normal sample.

These treatments of genetic data consider the number of observed copies for each gene in a specific state. Because of the high variability of gene expression data and the presence for many genes of a background expression level, multiple measurements are taken for each gene. The determination of the presence of a significant differential expression for a gene consists of comparing these measurements to a reference. Foreign patent references WO2011011426A2 to Shaffer and WO2007089583A2 to Akilesh, and U.S. Pat. No. 9,050,280 B2 to Vlassenbroeck also determine the expression or the numbers of copies of DNA or RNA/DNA.

The use of sequencing data in the above approaches is fundamentally different from determining genetic code alterations. Alterations are defined to include mutations, deletions, translocations and fusions—i.e. changes in the genetic code itself, measured with respect to a wild type background. In other words, the approaches provided by the prevailing art are concerned with detecting the number of copies of a gene, as opposed to the variants of the gene containing mutations to the genetic code itself. That is another shortcoming of the prior art that the instant invention addresses.

(D) Deep Sequencing, and Reducing the Search Space for Alterations

Another approach that has been proposed is to only identify genetic alterations (or calls) at a small subset of sites within the sites covered by the amplicon panel. NPL reference "An ultrasensitive method for quantitating circulating tumor DNA with broad patient coverage", dated April 2014 by Newman et al. and appearing in Nature Medicine, proposes performing deep sequencing and then search for mutations only at positions that are known to be present in the solid tumor. This approach is useful in monitoring response to a treatment, but because only a few (typically 2-4) alterations are monitored as a percentage of wild type DNA in blood plasma, the presence/emergence of new mutations is prone to be missed. It further expands the approach to looking at a few hundred positions where alterations are commonly found, but not across the whole amplicon space.

(E) High Sensitivity Detection Via Molecular Barcoding

Molecular barcoding has been described as a technique particularly suited to reducing the errors, and by extension the false positive (FP) rate. Briefly, the technology consists of the molecular labeling of each starting molecule in the sample, before any amplification and sequencing takes place. The molecular label typically consists of a unique DNA sequence that is added onto the end of the DNA fragments present in the primary sample. All molecules are then amplified and sequenced.

During the analysis, a specialized informatics pipeline is designed to recognize reads that have been generated from the same molecule, and then to collapse all of these reads onto the same sequence by a consensus operation. By doing that, it is shown that the equivalent error rate (error bases/kb) is dramatically reduced with respect to traditional sequencing outputs. The false positive rate is also significantly reduced, resulting in the ability to call mutations in the range of AF 1-2% with relatively high sensitivity and specificity. The reader is referred to NPL references "Reducing amplification artifacts in high multiplex amplicon sequencing by using molecular barcodes", dated August 2015 by Peng et al. and "Single molecule molecular inversion probes for targeted, high-accuracy detection of low-frequency variation", dated February 2013 by Hiatt et al. and Lanman et al. for further details.

Despite the above advantages, molecular barcoding methods have significant shortcomings that are barriers to its widespread adoption:

(i) The Need for a Specialized Chemistry and Bioinformatics Pipeline

Targeted sequencing and other sequencing approaches have been developed by the industry to a stage where there is a lot of content and clinical data available for certain libraries. Molecular barcoding requires different chemistries in the attachment of additional sequences (molecular barcodes) that preclude the use of certain amplicon libraries and make the development of new libraries more difficult.

Specialized bioinformatics are required for the specific barcoding method used. These routines/code are required to collapse the reads into individual molecule sequences. The related expertise adds cost to the commercial viability of these procedures.

(ii) The Need for Significantly Higher Read-Depths

Molecular barcoding works by obtaining a multitude of reads from a single molecule (or its complementary strand) and collapsing all of these reads into one that best represents the starting molecule. Because this process is imperfect, only a subset of molecules has the required reads per starting molecule to collapse onto the original sequence.

As a result, larger overall read-depths are required for resolving the same percentage mutant AF as compared to non-barcoded methods. For example, if 10 reads per unique molecular barcode are required, and the detection of a 0.1% AF variant (1/1000 molecules) is needed, at least a 10,000× read-depth will be required.

(iii) Loss of Sample Diversity During Barcoding Operations

The relatively low efficiency for the barcode attachment operation reduces the biological diversity of the starting DNA molecules entering the reaction. This leads to reduced sensitivity, especially where the starting number of molecular copies is low. Any molecule that does not ligate to a barcode in that initial step is excluded from the analysis. For instance, for a specific molecular barcoding approach, only less than 10% of molecules present in the starting target samples are labeled with a molecular barcode.

This significantly reduces the biological complexity of samples that are addressable using this method. This also substantially reduces the sensitivity for low AF variant detection. For more details, the reader is referred to NPL reference "Detection of ultra-rare mutations by next-generation sequencing" by Schmitt et al., dated, Sep. 4, 2012, and appearing in the Proceedings of the National Academy of Sciences (PNAS), volume 109. Even for other molecular barcoding approaches, the inclusion rate is typically 30-60% of the initial starting molecules, making this a difficult technique to implement where the starting numbers of copies are low.

Thus another shortcoming of the prior is that it does not teach techniques for performing high-sensitivity, low FP rate, detection of genetic mutations using samples where the AF percentage is low. For example, the prior does not teach techniques for mutant detection with high sensitivity and specificity where AF ranges include 0.01% to 0.1%, 0.1% to 0.5% or 0.5% to 1% AF.

Another shortcoming of the prior art is that it does not teach statistically comparing sequencing data from multiple replicate target samples, or target replicates, with sequencing data from multiple replicate reference samples, or reference replicates, for the detection of genetic code mutations.

Similarly, the prior art does not teach how to achieve the above sensitivity and specificity without requiring a prohibitively high sequencing depth and therefore at a prohibitively high operational cost.

OBJECTS OF THE INVENTION

In view of the limitations of the prior art, it is an object of the invention to provide ultra-sensitive methods and systems that are capable of detecting genetic mutations with high sensitivity and specificity, at very low allelic frequencies (AF), for example, ~0.01% AF with very high sensitivity above 0.999%.

It is another object of the invention to provide for non-invasive or minimally invasive testing procedures that use statistical testing to compare sequencing data from a set of target replicates with sequencing data from a set of reference replicates, for the detection of genetic mutations.

It is yet another object of the invention to provide a high-reliability and high-sensitivity testing protocol for oncology, NIPT, organ rejection and other diagnostic procedures, that does not require a prohibitively high depth of sequencing, and ultimately a high operational cost.

Still other objects and advantages of the invention will become apparent upon reading the detailed specification and reviewing the accompanying drawing figures.

SUMMARY OF THE INVENTION

The objects and advantages of the invention are secured by apparatuses and methods for detecting one or more genetic or genomic alterations/mutations in a target sample acquired from a donor/subject, e.g. a patient. The sample may be a solid tissue sample, or a liquid sample consisting of one of the various bodily fluids.

In addition to the target sample, a reference sample is acquired. The reference sample is known to be free of the genetic alteration(s) being detected. The reference sample is obtained from the same donor/subject, or alternatively acquired from another suitable donor/subject or a source of DNA standards. The target and reference samples are then divided into a set of replicates. Preferably, the number of target replicates is 3-6. Target replicates may be technical replicates or biological replicates, but originating from the same DNA sample. Reference replicates may be technical replicates or biological replicates.

When reference replicates are biological, they may be obtained from the same donor from whom the target DNA sample is acquired, or they may be obtained from one or more other donors. In the former case, the biological replicates are grown separately with measurements for each run taken at different points in time and under different conditions, as will be understood by those skilled in the art. The present invention is agnostic of how the target and reference replicates are eventually obtained, whether technically, biologically or otherwise.

At this stage, target and reference replicates are sequenced via DNA or RNA sequencing. The raw sequencing data may be acquired in the form of fastq file(s) or in any of the other (raw) sequence data file formats popular in the art. The raw sequencing data is then aligned and quality scored/filtered resulting in aligned and quality filtered target sequencing data originating from the target replicates and reference sequencing data originating from the reference replicates.

According to the invention, a suitable statistical test is then carried out on the target and reference sequencing data to determine the presence of genetic alteration(s) in the target. The distinguishing aspects of the invention include the incorporation of multiple target replicates as well as multiple reference replicates in the statistical determination of calls related to the genetic alteration(s) being detected.

The use of replicates, allows the invention to achieve very low False Positive (FP) rates at much lower Allele Frequency (AF) of the mutant material being detected, than possible through the techniques of the prior art. Preferably, the reference sequencing data and target sequencing data is stored in one or more target/reference profile arrays or tables or lists. Preferably, the one or more target/reference profile arrays or tables or lists reside in a database.

In a preferred embodiment, the statistical test used by the invention is based on a Student's t-test. In another embodiment, the statistical test is based on fitting the target and reference sequencing or measurement data to a negative binomial distribution. In yet another embodiment, the test is based on fitting the target and reference sequencing or measurement data to a Poisson distribution. The objective of statistical testing is to calculate a p-value. The p-value describes the probability that a mutation measurement is outside the reference distribution, indicating the existence of that mutation in the target sample. This p-value or a corresponding multiple hypothesis-adjusted p-value forms the basis for mutation identification.

In still another embodiment, the statistical test is based on the fold difference between the means of locus-specific corresponding measurements between the target and reference replicates. In related embodiments, the test is based on the comparison of the difference in the locus-specific measurement means of the target and reference replicates, with the corresponding locus-specific standard deviation or standard error. The comparison may employ standard deviation value of just the target replicates, reference replicates or both.

Preferably, the genetic alteration(s) detected by the invention are used in cancer diagnosis and/or in cancer treatment/therapies. Alternatively, the invention is used to diagnose an auto-immune disease. In still other variations, the invention detects the risk of an organ transplant rejection. In the case of Non-Invasive Prenatal Testing (NIPT), the invention is used to detect a genetic fetal abnormality or another fetal genetic trait. Still in alternative variations, the invention is used for pathogen diagnostics and to detect mutations in a pathogen, e.g. mutations in a viral or bacterial sub-population.

A molecular barcoding step is preferably utilized for the detection of mutation or genetic alteration. This entails applying a molecular barcode or label, consisting of a unique DNA sequence, onto the ends of the DNA fragments from the starting sample. Then all molecules are amplified and sequenced. A specialized informatics pipeline recognizes reads that have been generated from the same starting molecule.

The end result is a reduction of errors, and by extension the false positive rate, in the detection of mutations/alterations. Molecular barcoding may be combined with statistical treatment of replicates for even better performance. Reduced search space, as described in sub-section (D) of the background section, may also be combined with one or both of the techniques of molecular barcoding and of employing statistical replicates.

The invention also provides for a testing and analysis kit and associated methods, to facilitate its widespread practice at various sites. The kit preferably comprises a set of reagents needed to perform the sample preparation before sequencing, and a set of instructions or computer code capable of performing the statistical algorithms. The code may be provided on a storage medium such as a disk drive, USB drive, Secure Digital (SD) card, etc. or provided in the cloud.

The kit may also include human instructions on how to upload the experimental data to a cloud based (web) application and receive the resulting variants. The kit may also include targeted amplification chemistries with locus/position-specific background error rates for various targeted panels. Background error rates specific to popular sequencer equipment such as Illumina, Ion Torrent, etc. and associated processes may also be provided.

The kit preferably includes reagents for one or more of the following preparatory operations/steps: cell isolation, cell lysis, nucleic acid extraction and purification, DNA capture, liquid sample storage, shipping/transport and processing, reagents for the preferential capture of mutant sequences and reagents needed for targeted amplification of multiple samples/replicates originating from the same starting sample. The kit may further include reagents and consumables for circulating tumor cell enrichment from blood or other bodily fluids and/or reagents for free DNA extraction from blood, urine, or other bodily fluids. Furthermore, such a system may also include reagents and consumables for exosome extraction from blood, urine, or other bodily fluids.

It should be noted that the teachings of this disclosure apply equally to detecting alterations in any nucleic acid sequence, including a DNA or an RNA sequence. For ease of explanation however, the embodiments may employ DNA samples. But nonetheless, the reader is instructed to understand that the mutation detection techniques taught herein apply to such detection in any nucleic acid sequence whose target and reference replicates are being analyzed and compared according to the current teachings.

Clearly, the techniques and methods of the invention find many advantageous embodiments. The details of the invention, including its preferred embodiments, are presented in the below detailed description with reference to the appended drawing figures.

BRIEF DESCRIPTION OF THE DRAWING FIGURES

FIG. 3A-D show the measurements of the same variable under two different conditions X and X'. Where applicable the corresponding distribution of those measurements is also shown. Figures provide a comparison of traditional methods versus the instant invention for detecting the presence of a mutation.

Figure 4:
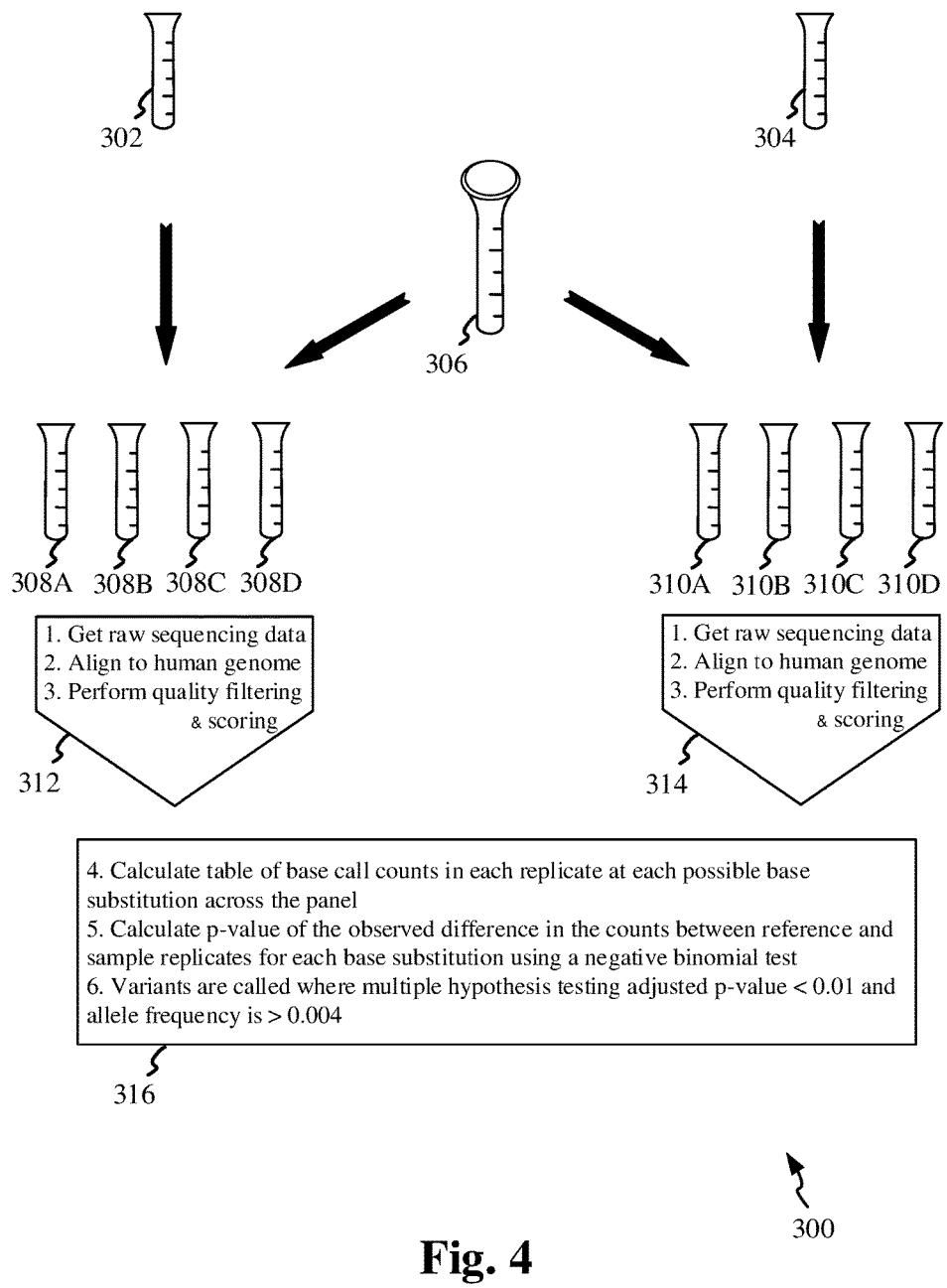

FIG. 4 shows an experimental setup with the processing and analytical steps according to the invention, employing four reference replicates and four target replicates.

Figure 5:
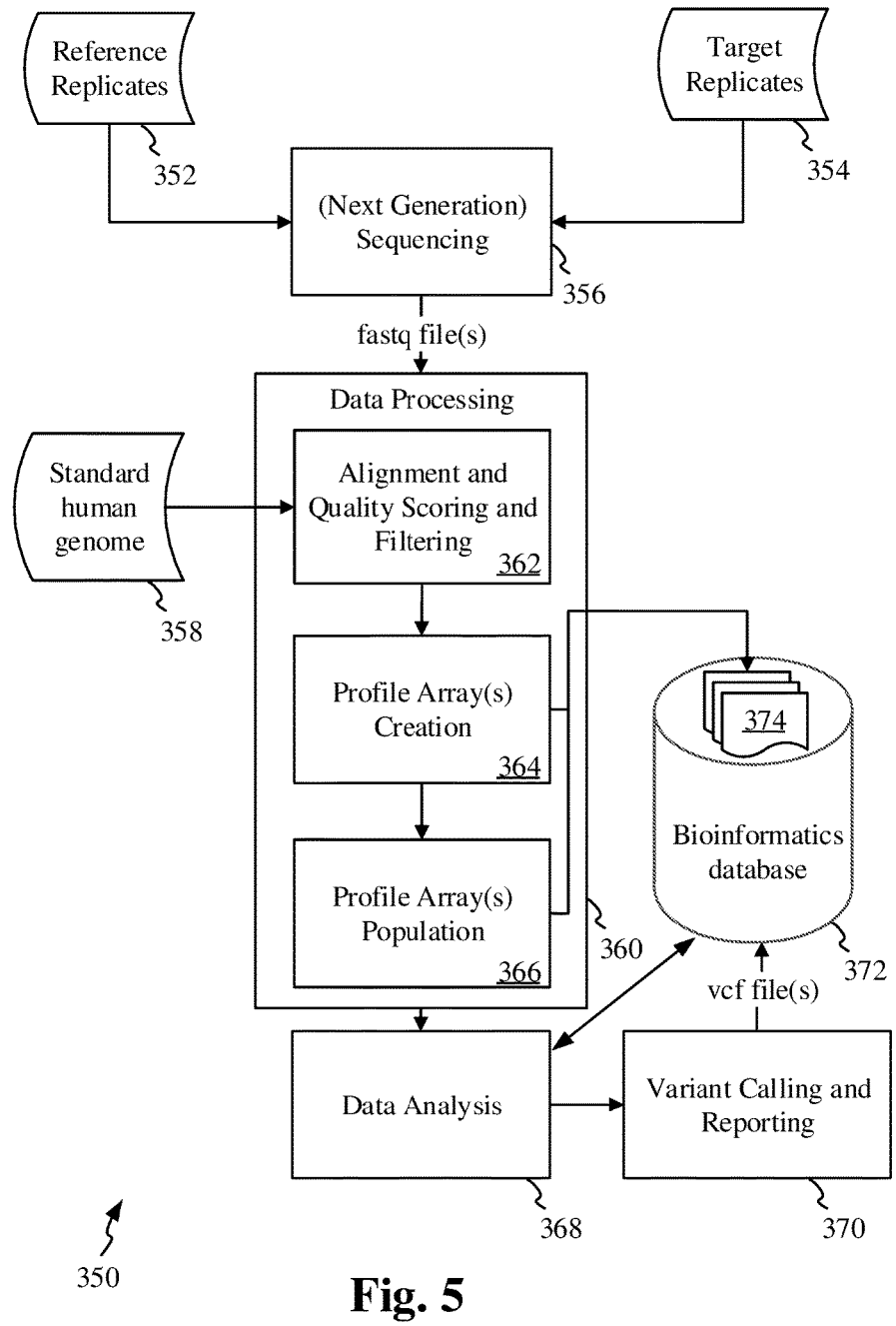

FIG. 5 shows an exemplary system architecture for performing the mutation diagnostic techniques of the invention.

Figure 6:
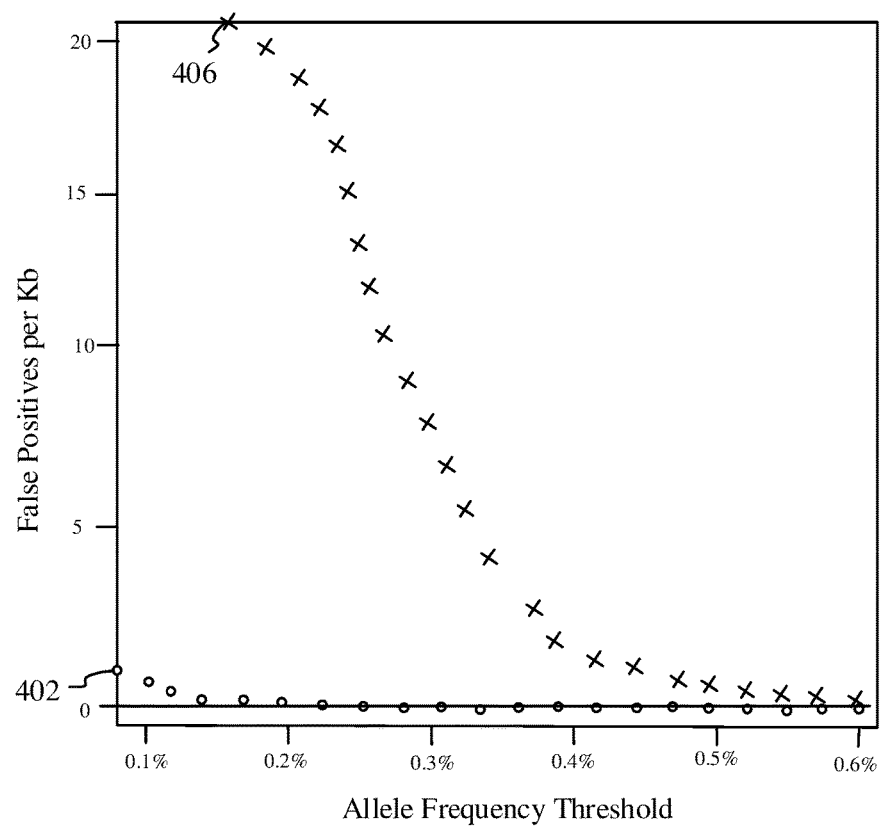

FIG. 6 shows in a comparison chart the efficacy of the results achieved by the invention at low Allelic Frequencies (AF) in comparison to the techniques of the traditional art.

DETAILED DESCRIPTION

The figures and the following description relate to preferred embodiments of the present invention by way of illustration only. It should be noted that from the following discussion, alternative embodiments of the structures and methods disclosed herein will be readily recognized as viable alternatives that may be employed without departing from the principles of the claimed invention.

Reference will now be made in detail to several embodiments of the present invention(s), examples of which are illustrated in the accompanying figures. It is noted that wherever practicable, similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

Figure 1:
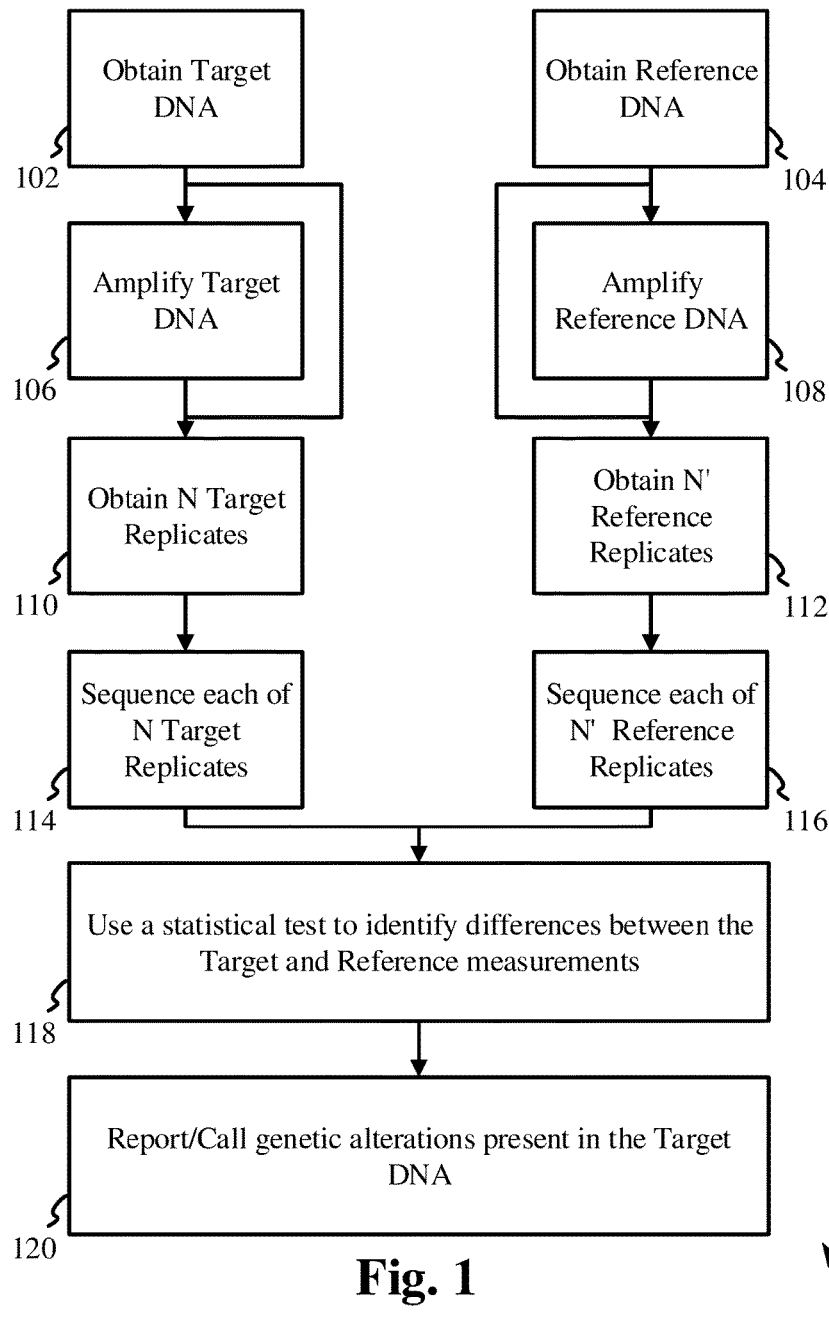
FIG. 1 shows an exemplary workflow/protocol for the detection of genetic mutations/alterations, according to the present invention.

The main aspects of the invention will be best understood by initially referring to the exemplary genetic mutation detection protocol 100 presented in FIG. 1. According to the invention, a target sample, either liquid or solid, is obtained from a donor in step 102. The target sample, also simply referred to as the target or the sample, is presumed to contain a genetic alteration or mutation that is desired to be detected according to the techniques taught herein. The donor may be a patient or another subject undergoing testing for any number of reasons, including clinical trials. The patient may be human or non-human.

In addition, another sample consisting of non-tumor normal material is also obtained from either the same donor or a reference source in step 104. The sample in step 104, called the reference sample, also simply referred to as the reference, is known to be free of genetic alteration(s) or mutation(s) being targeted or detected. In cases where the "matched normal" is not available from the same donor or the same clinical patient, then another "normal" DNA control sample may be drawn from another matching donor with a healthy tissue or bodily fluid known to be devoid of somatic mutations. Still otherwise, the normal DNA control sample may be derived from a source of DNA standards. Examples of such DNA standards include human cell line derived DNA, DNA extracted from healthy human tissues, human DNA standard reference materials, or synthetic DNA overlapping the regions of interest.

The target and reference samples thus obtained are then amplified in steps 106 and 108 respectively. As indicated in FIG. 1, steps 106 and 108 are optional. This is because, the amplification of target and/or reference samples may or may not be required, depending on the concentration of the altered/mutant genetic material content (e.g. tumor) as compared to the overall amount of the solid or liquid sample obtained in steps 102 and 104 above. Steps 102, 106, 110 and 114 may be carried out singly or in combination, and independently of steps 104, 108, 112 and 116 in protocol 100 of FIG. 1. Examples of liquid sample obtained from the patient include blood or blood components, urine, stool samples, pleural fluid, ascites, sputum, etc. Solid sample may be tissue from the mutation affected area of the body.

Any appropriate technique chosen from the various nucleic acid amplification techniques available in the art may be employed for the optional amplification steps 106 and/or 108. The invention is agnostic of such amplification techniques. A non-exhaustive list of such techniques is Polymerase Chain Reaction (PCR), Ligase Chain Reaction (LCR), Loop Mediated Isothermal Amplification (LAMP), Nucleic Acid Sequence Based Amplification (NASBA), Strand Displacement Amplification (SDA), Multiple Displacement Amplification (MDA), Rolling Circle Amplification (RCA), Helicase Dependent Amplification (HDA), Ramification Amplification Method (RAM), etc.

After the optional amplification steps 106, 108, the target and reference samples are replicated in steps 110 and 112 respectively. Preferably, the number of target replicates thus obtained are 3 to 4, and the number of reference replicates thus obtained are 3 to 6. In other variations, the number of target and/or reference replicates is much larger. The number of target and reference replicates are indicated by N and N' respectively in FIG. 1. Those skilled in the art will understand that replication of the target and reference samples can be achieved by simply dividing the respective target and reference samples into the desired number of N and N' target and reference replicates respectively.

The above process is called technical replication and the replicates thus obtained are called technical replicates. In order to have the desired concentration of genetic material in the technical replicates, an amplification step such as step 106 and/or step 108 may be necessary. Note, that instead of or in addition to the amplification steps 106 and 108, amplification may be performed on the replicates themselves as obtained from steps 110 and 112, and after the respective target and reference samples have been divided/replicated.

An alternative to technical replication is referred to as biological replication. Biological replicates have biologically distinct composition, and are typically obtained from different procedures. When derived from the same reference donor, they are grown separately into the desired number of replicates with measurements typically taken at different points in time and under different conditions. Usually costlier and requiring more time, biological replicates are generally considered to be statistically superior to technical replicates because of their genetic diversity. The choice between technical and biological replicates is a trade-off based on cost, expediency, accuracy of results and other factors.

The present invention is agnostic of the way the replicates are obtained in steps 110 and 112, and its techniques apply equally to the various implementations of protocol 100 of FIG. 1. Of course, it is entirely possible to choose technical replication for target sample and biological replication for reference sample or vice versa. Similarly, it is possible to choose whether or not DNA amplification is required for the target sample independently of the reference sample. The number of such implementation choices of protocol 100 within the scope of the invention will be apparent to a person of ordinary skill.

Returning to FIG. 1, the desired number of target and reference replicates are obtained in steps 110 and 112. At this stage, each of the target and reference replicates are sequenced. Note that prior to sequencing, additional steps are also typically carried out on the replicates. These include lysing of the cells of the replicates to obtain their corresponding cell-free DNA. Furthermore, a purification and enrichment step may also be carried out on the cell-free DNA of target and/or reference replicates, so that the desired concentration of genetic material is achieved prior to sequencing. For a discourse on such techniques and similar topics, the reader is referred to U.S. patent Ser. No. 10,167, 502 B2 issued on Jan. $1^{st}$, 2019.

Those skilled in the art will also appreciate the vast number of choices available for DNA sequencing approaches, including Next Generation Sequencing (NGS). There are a number of such DNA sequencing techniques and the respective equipment available for that purpose, e.g. Illumina, Ion Torrent, etc. The raw sequencing data generated by such equipment would typically be collected and stored in a file in one of the popular sequence file formats, such as a fastq file format, etc. The above techniques are well known in the art and will not be delved into detail in this disclosure.

Sequencing steps 114 and 116 of FIG. 1 result in the collection of sequencing data from the target and reference replicates respectively. This data is collected after the standard alignment and quality scoring/filtering steps of DNA sequencing known in the art. Once the raw sequencing data obtained above has been aligned and quality scored, we then refer to this data as target and reference sequencing data for the purposes of this disclosure. In other words, we reserve the terms "target sequencing data" and "reference sequencing data" to sequencing data that has already been genome-aligned and quality scored and filtered.

Of course, that means that we refer to the aligned and quality scored/filtered sequencing data originating from the target as target sequencing data, and we refer to the aligned and quality scored/filtered sequencing data originating from the reference as reference sequencing data. The techniques for alignment and quality scoring and filtering of raw sequencing data are well known in the art and will not be delved into detail in this specification. Once target and reference sequencing data from N and N' target and reference replicates respectively has been collected after steps 114 and 116 respectively, an analysis step 118 is carried out as shown in FIG. 1.

Target sequencing data and reference sequencing data may be stored in one or more files, and analyzed accordingly by one or more processing, analysis and/or reporting modules. As will be explained later, FIG. 5 shows an exemplary computer design/architecture for an implementation of the embodiments according to the invention. The vast number of system design choices and configurations for practicing the instant invention will be apparent to a person or ordinary skill in the art.

Step 118 of protocol/workflow 100 utilizes a suitable statistical test to determine the genetic differences between the target and reference sequencing data, or sets of measurements, from the respective target and reference replicates obtained above. Genetic differences that satisfy an appropriate statistical measure/criteria of significance and are determined to be in the original target sample in step 102, are then reported, or called, as genetic/genomic alteration(s) detected by protocol 100. This reporting is performed in step 120, which can be combined with the analysis step 118 if desired.

As already stated, there are many possible variations of the implementation of protocol 100 of FIG. 1. For example, reference sample may be sequenced once and sequencing data obtained from the reference sample may be used for statistical processing for each target replicate in step 118. In other words, reference DNA in step 104 may not be formed into replicates. Instead, in a single "run" of the experiment, sequencing data collected from reference DNA may be used in the statistical test in step 118 to determine the genetic differences between the target replicates and reference DNA.

However, having reference replicates has the advantage of substantially improving the results of statistical processing in step 118 as will be further taught below. Alternatively, reference sequence data may be obtained at a different time and place from target sample data and then used afterwards during the analysis of a large number of target samples according to the teachings provided herein. Obviously, in any variation, amplification step 108 of reference DNA can be invoked as needed.

Using the techniques of protocol 100 of FIG. 1 according to the invention, it is possible to achieve a much higher sensitivity and specificity than the approaches available in the prior art. Typical sequencing experiments for the detection of genetic abnormalities have a floor of 1-3% allele frequency (AF). As already explained in the background art section, in most setups of the traditional art, solid tumor sequencing calls only go down to 3-5% AF. For a variety of sample types in practice however, abnormalities are present at much lower percentages, down to 0.01% AF in bodily fluids. Therefore, it is desirable to eliminate noise and detect true abnormalities present at or below 0.1% AF, and down to at or below 0.01% AF. The techniques of the instant invention enable us to do that.

The noise present in typical experiments includes DNA replication errors (introduced during whole genome amplification or during targeted amplification) as well as sequencing errors. Some of these errors are recurrent. In other words, there is a higher probability of the wrong base being incorporated or a misread at a certain site/position/locus/location. Homopolymer errors are one example, where repeated bases cause errors at the ends of the homopolymer sequence. Regardless of the source of these errors, they are characterized by the fact that they are likely to be present at similar levels in repeated experiments, irrespective of the provenance of the starting DNA sample.

In order to remove these recurrent errors, the instant techniques sequence a reference sample, or a set of reference replicates, and use sequencing data from the reference sample/replicates to establish a background mutation rate. The background mutation rate is also sometimes referred to as a background error rate. That background error/mutation rate is established at each locus/site or around each sequence feature.

Figure 2:
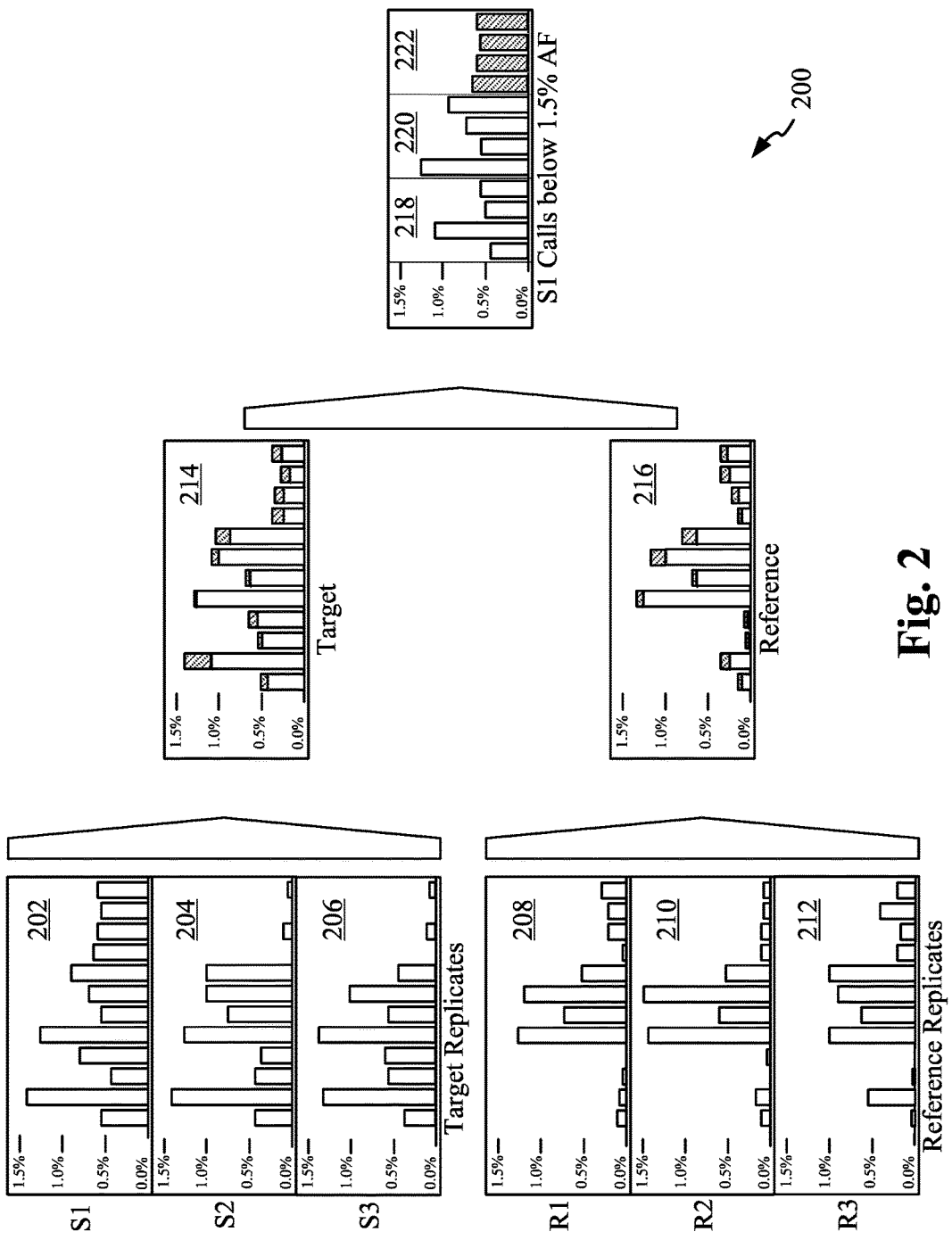
FIG. 2 shows a diagnostic and detection setup according to the invention, employing three target sample replicates and three reference sample replicates.

To understand this better, let us consider the diagnostic setup illustrated in FIG. 2 according to the invention. This scenario has three reference replicate sequencing runs R1, R2 and R3, represented by numerals 208, 210, 212 respectively, and originating from a given reference DNA sample. Put differently, reference replicate runs R1, R2, R3, or simply stated reference replicates R1, R2, R3, are represented by numerals 208, 210 and 212 respectively. Each replicate run R1-R3 has sequencing data for each of 12 loci shown by the 12 bars of the bar graphs.

The sequence data obtained from reference runs R1-R3 is then assembled into a reference background error/mutation dataset 216 with mean observed mutation rate and standard deviation at each of the 12 loci. Note that we may also refer to background error or mutation dataset 216 as simply background error or mutation rate 216, or even more simply as reference background 216. As already stated, locus-specific reference background 216 as shown in FIG. 2, is established specific for each locus i.e. loci 1-12 in the example shown.

According to the invention, a number of target sample replicates are also analyzed and statistically compared against reference background 216. Preferably, the number of such target sample replicate runs is 3-6. Still preferably, the number of reference replicate runs is also 3-6. In the example shown in FIG. 2, three target replicates S1, S2, S3, and three reference replicates R1, R2, R3 are used. Target replicate runs S1, S2, S3, or just simply target replicates S1, S2, S3, originating from the same starting target DNA sample, are represented by numerals 202, 204 and 206 respectively.

Sequencing data from target runs S1-S3 is collected into a target/sample/mutant dataset. As already mentioned, the sequencing data as shown in FIG. 2 is post genome-alignment and quality scoring and filtering. Sequencing data from runs R1-R3 and S1-S3 is then used to compute an appropriate locus-specific statistical average and a measure of variability from it, for both target/mutant dataset 214 and reference/normal dataset 216 used in the experiment. For the reference dataset 216, these locus-specific values constitute the locus-specific background error or mutation rate/dataset mentioned above.

The statistical average may be mean, median, mode, range, etc. The variability may be measured using standard deviation, median absolute deviation (MAD), Standard Error or the Mean (SEM), etc. Exemplary datasets 214 and 216 in FIG. 2 show the mean AF and corresponding SEM values at each locus for replicates S1-S3 and R1-R3 respectively. Specifically, the mean AF and Standard Error of the Mean (SEM) are shown respectively by unhatched and hatched portions of the corresponding measurement bars. Dataset 214 is then compared to reference/background mutation dataset 216.

Based on the results of the comparison, a selection of true positives from a mix of true and false positives is made. The comparison is done using any suitable statistical tests/techniques, in order to determine the true positive final calls associated with target replicates S1-S3. These true positive calls are associated to the original target sample. The example of FIG. 2 on the right hand side shows the calls from target replicate S1 statistically analyzed against reference background 216. The analysis illustrates the advantages of utilizing all replicate sample runs (202, 204, 206) as opposed to just one replicate run, S1.

Specifically, AF measurements at each locus of multiple target replicates (202, 204, 206) are utilized to form a resultant target/mutant dataset, an example of which is shown by numeral 214 in FIG. 2. Similarly, AF measurements at each locus of multiple reference replicates (208, 210, 212) are utilized to form a resultant reference/background dataset, an example of which is shown by numeral 216 in FIG. 2. According to the invention, the statistical comparison of the resultant target/mutant and reference/background datasets produces much more robust results than otherwise possible by using just a single target sample and/or a single reference sample.

Exemplary results from the above analysis are shown on the right hand side in FIG. 2 as composed of true positives 218, recurring artifacts 220 and stochastic errors 222 shown by hatched pattern. Using the techniques of the invention, thus one is able to detect true positive calls below allelic frequency (AF) of 1.5% as shown in the figure. This is a clear advantage of the instant invention over the prior art in its specificity and sensitivity to perform general screening tests of cancer and other diseases from liquid biopsies. Note that while the techniques of the invention are particularly suited to liquid biopsies, they just as well apply to solid biopsies and other types of liquid/solid samples.

It should be understood, that in the embodiments explained above, the use of statistical averages and corresponding variabilities are examples of specific implementations. Similarly, the use of appropriate statistical comparisons/tests for comparing the above values for target and reference samples are exemplary of certain embodiments. Indeed, in addition to the above examples, the invention admits of a number of specific statistical methods/approaches for making mutation calls in target samples versus the reference/background as will be taught below.

In the context of the embodiments of FIG. 2, these statistical approaches function by comparing the background "noise" or background error/mutation rate present in the reference runs, as captured in the exemplary dataset 216, to an accurately determined allelic frequency (AF) present in the target replicates. For abnormalities where the AF is small, the accuracy of the target AF at that particular locus is best determined by performing multiple sequencing runs starting from the same target/sample DNA, e.g. S1-S3 in FIG. 2. A run is defined to include some or all of the amplification steps, for example targeted amplification using an amplicon panel, as well as the required sequencing steps, including sample barcoding, data acquisition and demultiplexing.

The output of each run may be a Variant Call Format (vcf) file, or any other familiar file type containing sequence data with variant information. In the preferred embodiment of the invention, at least 3 sample replicates (e.g. S1-S3 in FIG. 2) are provided to the statistical algorithm used. Note that certain errors, like replication errors occurring during early rounds of replication may appear at relatively high AF in one sample i.e. sample S1 variants at loci 9-12 in FIG. 2, but are not repeated in sample replicates S2 and S3. This is due to the stochastic nature of these errors. These stochastic errors 222 are easily differentiated from true positive calls 218 as shown.

Further, note that in the example of FIG. 2, true positive variants at loci 1-4 appearing at elevated AF in all sample replicates (S1-S3) on the respective bar graphs, are significantly different from measurements/reads found at the same locus in reference samples R1-R3. Of course the same is not true of variants at loci 5-8, which represent recurring artifacts. In other words, at loci 5-8, measurements/reads in both the reference samples R1-R3, and target samples S1-S3 have a recurring pattern. These are representative of recurring artifacts 220 that are differentiated from the eventual true positive calls 218. To summarize, according to the invention as taught by the exemplary demonstration in FIG. 2, true positive calls 218 at low AF are effectively detected and distinguished from recurring artifacts 220 and other stochastic errors 222.

The above detection of true positive calls at low AF can employ a suitable statistical test. The statistical test may further use a statistical measure of significance, based on which calls are made. The statistical test can take a number of forms. In one embodiment, the fold difference is used for comparison. Specifically, a statistical average x of the locus-specific target measurements is computed. Also, the same statistical average y of the corresponding locus-specific reference measurements is computed. A call is made for the locus if the fold difference between x and y is greater than a certain statistical measure of significance or threshold. The statistical average may be mean, median, mode, range, etc.

In the example of FIG. 2, sample variants S1-S3 at loci 1-4 will be called because the means of the measurements at loci 1-4 in targets S1-S3, are significantly more than the corresponding means at loci 1-4 of the references R1-R3. Note again, that in this disclosure, we may refer to target sample replicates or target replicates, as simply targets. Similarly, we may also refer to reference sample replicates or reference replicates, as simply references.

In other embodiments, the statistical test compares the locus-specific difference of the mean between the targets and references measurements with the locus-specific standard deviation of the targets and reference measurements. For example, the test may require that the locus-specific difference of the means is greater than n times the sum of the locus-specific standard deviations. In additional variations, the statistical test compares the locus-specific difference of the mean between the targets and references measurements with the locus-specific SEM of the targets and/or samples measurements. For example, the test may require that the difference of the means is greater than n times the sum of the SEM values.

Advantageously, a Student's t-test is used to determine the significance of the difference between the sample and reference measurements. A Student's t-test may be used to determine if the variant data from target samples is statistically different from the reference data, under the null hypothesis that the sample data is not statistically different from the reference data. If the p-value determined by the t-test is less than a cutoff/threshold α (typically 5%), indicating that the null hypothesis is false, then a call is made at that locus, otherwise no call is made. Let us explore this and related embodiments through the following example.

First note trivially that in the following explanation, the relationship between p-value and cutoff α for a call to be made is that of < or less than inequality. In other words, if p-value <α then the call is made, otherwise if p-value ≥α then the call is not made. However, depending on the choice of the value of cutoff/threshold α, the relationship could be just as easily ≤ or less than or equal to relationship, with the call being made when p-value≤α, and the call not being made when p-value >α.

Let us now also understand that during DNA sequencing at each location in the sequenced portion of the genome, a particular read contains one of 4 nucleotide bases: A, T, G, or C. Therefore, at each location there are 4 possible nucleotides in each read. During sequencing, the number of reads containing a certain nucleotide base, or more simply just a base, at each position is recorded. Alternatively, or in addition, the percentage of reads of a base at each position out of the total read-depth or depth of coverage, is recorded. This latter value is also referred to as digitized allelic frequency, or allelic frequency, or AF for short.

Because the number of reads of a genomic region or locus can vary from one experiment to the next, or from one genomic region or locus to another, the AF value serves as a more normalized or scaled indicator of the measurement. AF value is expressed as ((total number of reads of a base at an index i/total read-depth (or depth of coverage) at index i) 10,000.

Example 1

This exemplary process entails assembling a profile for the target sample in the form of an allelic profile array or table or a set of lists, also termed simply as a profile array/table of observations/reads. The array could also be implemented as a linked-list, C/C++ "structs" or a Java class, or any other suitable data structure constructs known to those familiar with the art of computer software and programming.

Let us assume that we are analyzing a sequence with a length of 10 base-pairs (10 bp). Thus the profile array for the target, or target profile array, will contain a set of 40 possible base read numbers, for the 4 possible bases at each position/locus. As mentioned above, the read number or just simply a read or a measurement or an observation at a locus, refers to the total number of reads of a base at that locus, and/or the percentage of reads of the base at that locus out of the total read-depth i.e. AF.

The target profile array/table X is then represented by the value of the read/measurement for each possible base at each possible position. Thus X: $X_i = X_1, X_2 \ldots X_n$ where n=40 in this example, and i is a particular base nucleotide at a particular locus/position in the sequence. The index i is referred to as the allele index, or allelic index, because we are concerned with finding mutations in individual base-pairs of the gene/allele.

If the measurements using the above process are done in m independent experiments using m target replicates derived from a target sample, then the target profile is represented by X: $X_{ij} = X_{11}, X_{12}, X_{21}, X_{22}, \ldots X_{2m}, \ldots X_{n1}, X_{n2}, \ldots X_{nm}$ where i is the allelic index and j is the target replicate number. Preferably m=3. An exemplary target sample may be a liquid biopsy containing tumor material.

Using a similar process, we also create a reference profile in the form of a reference profile array/table X': $X'_{ij}$ where the measurements are made starting from a set of m' reference replicates derived from a reference sample. In one embodiment, at each allelic index i, the set of target sample measurements X: $X_{ij}$ are compared to the set of reference measurements X': $X'_{ij}$.

Table 1 is a representation of the target profile or target profile array or target profile table, obtained in the above example. Note that only the first 8 out of the 40 allelic index values and the corresponding measurements are shown for clarity. These 8 values are representative of the 4 possible values for bases A, T, C, G at the first two loci of the 10 bp DNA sequence of the above example. These two loci are positions 1113 and 1114 of chromosome 1, as provided in Table 1 below.

We may refer to the individual cells under columns M1-M3 of target profile/array X as the target read numbers, each cell containing a target read number obtained from one of 3 replicates M1, M2, M3 corresponding to a given value of the Allele index column i. As explained and as shown, each allele index value i in turn corresponds to a value in the Position/Mutation column. Analogously, we would have reference read numbers under respective cells of M1', M2', M3' columns of the reference profile array/table X' explained above. As would be apparent, that in this embodiment, the target read numbers and reference read numbers constitute the target sequencing data and reference sequencing data respectively.

Note that instead of a DNA sequence, the example below and the associated embodiments can also be used to analyze any other nucleic acid sequence, including an RNA sequence. Of course, such analysis will be based on acquiring multiple target replicates of the nucleic acid sequence and comparing against multiple reference replicates according to the invention. Corresponding adaptations to the current examples and associated embodiments, e.g. positions and the types of the nucleotides, etc., will be apparent to one with ordinary skill in the art.

TABLE 1

| Allele index | | Quantity Measurements | | |
|---|---|---|---|---|
| i = | Position/Mutation | M1 | M2 | M3 |
| 1 | ch1; 1113/A | $X_{11}$ | $X_{12}$ | $X_{13}$ |
| 2 | ch1; 1113/T | $X_{21}$ | $X_{22}$ | $X_{23}$ |
| 3 | ch1; 1113/G | $X_{31}$ | $X_{32}$ | $X_{33}$ |
| 4 | ch1; 1113/C | $X_{41}$ | $X_{42}$ | $X_{43}$ |
| 5 | ch1; 1114/A | $X_{51}$ | $X_{52}$ | $X_{53}$ |
| 6 | ch1; 1114/T | $X_{61}$ | $X_{62}$ | $X_{63}$ |
| 7 | ch1; 1114/G | $X_{71}$ | $X_{72}$ | $X_{73}$ |
| 8 | ch1; 1114/C | $X_{81}$ | $X_{82}$ | $X_{83}$ |

As will be explained further below, the above profile array is useful in determining Single Nucleotide Variants (SNVs) in the exemplary 10 bp long DNA sequence, of which rows corresponding to only the first 2 bp are shown in Table 1 for clarity. However, a practitioner of ordinary skill can conceive using larger arrays or tables that contain read numbers for other DNA aberrations such as deletions, insertions, translocations, etc. According to the key aspects of the invention, the determination of genetic mutations in the target sample is made based on comparing target profile X: $X_{ij}$ with reference profile X': $X'_{ij}$ and determining if and how different they are from one another.

Such a comparison may be made by comparing respective values of the two arrays/tables. In other words, by comparing $X_{1j}$ and $X'_{1j}$ at allelic index i=1, and comparing $X_{2j}$ and $X'_{2j}$ at i=2 and so on. In this example, let us assume that m=m' for ease of explanation, however the current teachings readily extend to experimental setups where m≠m', as will be appreciated by a skilled reader and as will be further explained below. Note that in alternative variations of the present embodiment, reference profile array and target profile array may be combined into a single allelic array or still alternatively, further broken up into more arrays or lists containing individual observations from each replicate.

A variety of such design choices and their pros and cons will be apparent to a person of ordinary skill in the art. We will continue to use the above example of separate reference and target profile arrays, with the implicit understanding of the wider applicability of the present teachings to various alternative structures for the reference and target profiles taught herein.

In the preferred embodiment, a statistical test is applied for measuring the statistical significance of the difference between the target and reference profiles. An exemplary statistical test is the Student's t-test given by the following equation for comparing our two groups of measurements X and X':

$$t = \frac{\overline{X} - \overline{X}'}{s_{XX'} \cdot \sqrt{\frac{2}{m}}}, \quad \text{Eq. 1}$$

$$\text{where } s_{XX'} = \sqrt{\frac{s_X^2 + s_{X'}^2}{2}}.$$

Here $s_{XX'}$ is the pooled standard deviation for samples X and X'. A commonly used expression for pooled standard deviation $s_{XX'}$ is given by:

$$s_{XX'} = \sqrt{\frac{(m-1)s_X^2 + (m-1)s_{X'}^2}{(m-1) + (m'-1)}} \quad \text{Eq. 2}$$

where sample variances $s_X^2$ and $s_{X'}^2$ are given by:

$$s_X^2 = \frac{1}{m-1} \sum_{i=1, j=1}^{i=n, j=m} (X_{ij} - \overline{X})^2 \text{ and } s_{X'}^2 = \frac{1}{m'-1} \sum_{i=1, j=1}^{i=n, j=m'} (X'_{ij} - \overline{X}')^2.$$

The above form of Student's t-test is applicable when X and X' behave as normal or Gaussian distributions, and are assumed to have the same variance and same sample size m=m'. However, a person of ordinary skill in the art will recognize the alternate forms of the t-test. These include t-tests for unequal sample sizes i.e. "unpaired" or "independent samples" t-tests. Still other forms of the t-test include t-tests for unequal variances, for example, Welch's test. Still other forms include t-tests for non-normal (non-Gaussian) distributions. Still other tests used to compare a group of measurements to an expected measurement distribution can also be readily envisioned.

In a typical fashion, the t parameter above is used to determine the probability p (or p-value) that the two groups of measurements X and X' are similarly distributed. More specifically, a null hypothesis is defined which assumes that the two distributions to which measurements X and X' belong to, have the same mean. A cutoff measure of significance α is then used to accept or reject the null hypothesis.

In other words, statistical measure of significance a is used to determine which group of target sample measurements $X_{ij}=X_{i1}, X_{i2}, \ldots X_{im}$ in our target profile array explained above (see Table 1), are significantly different from the group of reference measurements $X'_{ij}=X'_{i1}, X'_{i2}, \ldots X'_{im}$ by testing if p-value <α. For example, let us consider the third row of Table 1 above (i.e. i=3) for the above statistical test. If p-value based on t statistic computed in Eq. 1 above is $<\alpha$ for i=3, then a call is made for base-pair ch1;1113/G.

Note that it is unlikely but possible for multiple calls to be made at the same location in a nucleic acid (DNA/RNA) sequence. This is because multiple mutations may be present at the same location in the target sample, for example, due to DNA originating from different cells of the target sample. Continuing with our example of Table 1 above, if p-value $<\alpha$ for i=3 and i=4, then calls will be made for base-pairs G and C at location ch1;1113. The present invention is able to make such multiple calls, because it stores each possible combination of the nucleotide base read in the nucleic acid sequence and corresponding allele index i. As taught, these values are stored in one or more allelic profile arrays, an example of which is shown in Table 1.

The associated techniques for selecting cutoff $\alpha$ and for computing the p-value from the t statistic, are well known in the art of statistics and will be familiar to a person of ordinary skill. Examples of such techniques include the p-value tables known in the art.

A key distinguishing feature of the instant invention as compared to the statistical techniques used in gene expression analysis is that the present invention applies statistical testing to individual alleles/genes at the base-pair level (see Table 1). Explained further, gene expression analysis is concerned with the number of copies of entire genes expressed at the DNA or RNA level. In contrast, the instant techniques detect mutations of the genetic code at the base-pair level within the alleles/genes, as opposed to the copy number variations (CNV) of the entire genes themselves.

A gene/allele, of course, may consist of a few, dozens, hundreds, thousands or more base-pairs. As such, the 'aperture' of the instant statistical measurement techniques for mutation detection is much more fine-grained than the prevailing techniques of gene expression analysis. This is a major improvement of the invention over the techniques of the prior art. The present invention is not concerned with the number of copies of the base-pairs or alleles/genes, but rather the changes in the alleles/genes as a result of the mutations in their constituent base-pairs. This is a major improvement over the prevailing techniques.

Explained yet differently, notice that Table 1 consists of the number of observations of base-pairs at individual locus/locations 1113 and 1114 in chromosome 1. That is because the instant invention addresses finding mutations/changes in the base-pairs as opposed to the number of copies of the genes or base-pairs. The base-pairs may be the constituent base-pairs of the alleles/genes themselves. On the other hand, the prevailing techniques are only concerned with the number of copies of the genes. As already stated, each allele/gene may consist of any number of base-pairs.

Let us further explore the superior performance of the present techniques over the prior art, using the illustrations of FIG. 3A-D. First, as will be apparent by now, the above embodiments of the invention determine the probability (expressed by the p-value) that two sets of measurements X: $X_1$-$X_m$ and X': $X'_1$-$X'_m$ belong to two distributions that have the same mean. Because, otherwise, they would not be similarly distributed, and be indicative of a mutation call. Therefore, a typical test is to require the p-value to be below a very low set threshold $\alpha$ i.e. requiring the probability that measurements X and X' are similarly distributed to be very low if a call is to be made.

Figure 3A:
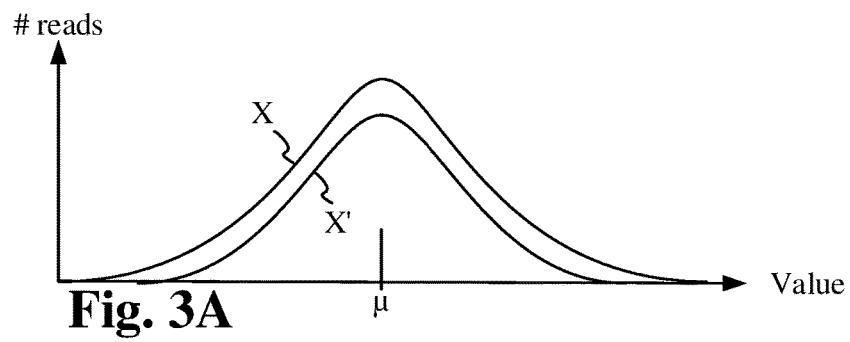

FIG. 3A shows the normal (Gaussian) distributions of two sets of measurements X' and X that have the same mean value $\mu$. It is presumed that the two sets of measurements are made under two different conditions as per above teachings. For example, a set of reference replicates is employed for measurements X and a set of target replicates is employed for measurements X'. Note that the X-axis represents the value of the measurement/read/observation in FIGS. 3A-D, and the Y-axis represents the number of individual measurements/reads/observations with a certain value corresponding to X-axis. Unsurprisingly, the number of reads centered around the mean $\mu$ are the highest.

Figure 3B:
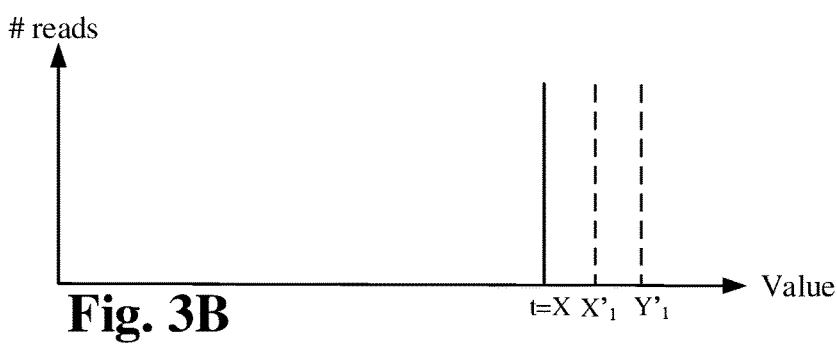

In the example shown in FIG. 3A, distributions X' and X have the same mean, indicating that there is no alteration in measurements X' with respect to the background/reference X. Prevailing techniques of mutation detection yield significantly worse performance than the present invention, because they fall in one of the following categories (1) or (2) or some combination thereof:

(1) Use of a simple universal threshold t for making all mutation calls. Threshold t is chosen as a single reference measurement t=X. Then if a certain target measurement $X_1'>t$, then the mutation is assumed to be positive and a call is made for measurement $X_1'$. The same threshold t is applied across the board for all mutations. As illustrated in FIG. 3B, threshold t is used to decide calls for one mutation in measurement $X_1'$ and for a second mutation in a different measurement $Y_1'$.

(2) The use of a threshold t as a background reference level which is some amount of standard deviation $\sigma$ from mean value $\mu$ of the background/reference X set of measurements. If a target measurement $X_1'>t$ then a call is made. This is illustrated in FIG. 3C with t=1.7$\sigma$ more than mean $\mu$ of reference measurements X.

Figure 3C:
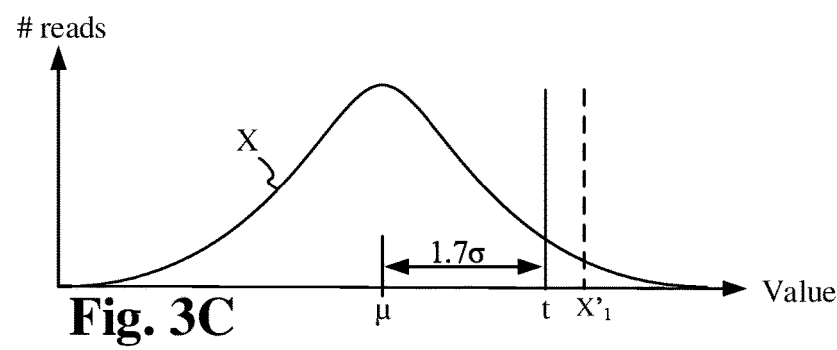

In contrast, as opposed to a single measurement $X'_1$ (or $Y'_1$) of FIG. 3B, and a single measurement $X'_1$ of FIG. 3C, the instant techniques fit multiple reference measurements X: $X_{1-m}$ to a statistical distribution, and also multiple target measurements X': $X'_{1-m'}$ to a statistical distribution. Preferably, m=m'=3, however as discussed, the invention admits of other variations including where m≠m'. The resulting comparative and statistical analysis of these two distributions X and X' yields significantly improved sensitivity and specificity of the results.

Figure 3D:
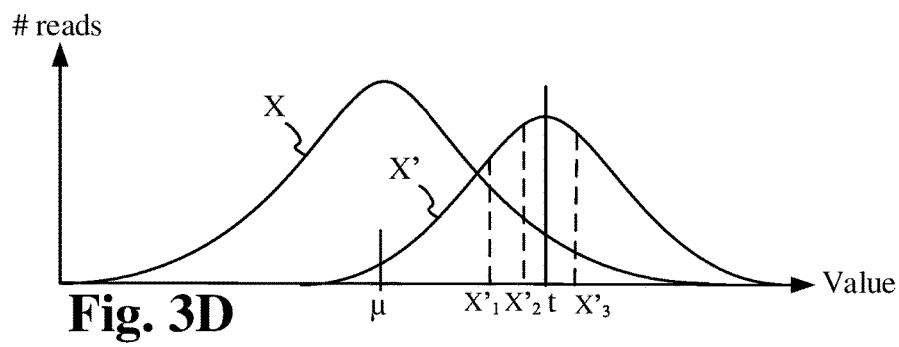

Specifically, a null hypothesis assumes that reference measurements X and target measurements X' are similarly distributed. In other words, they belong to normal distributions with the same mean $\mu$ (see FIG. 3A). Then a p-value of the probability of the null hypothesis is computed. If the p-value is sufficiently low, the null hypothesis is rejected and a call is made. FIG. 3D illustrates this scenario and the superior call quality according to the instant techniques.

Note, that even though the prevailing techniques are only concerned with taking one measurement $X_1'$ as explained above, additional measurements $X_2'$ and $X_3'$ of FIG. 3D of the present invention would not have been called under the prevailing regimes of FIG. 3B-C. In contrast, $X_2'$ and $X_3'$ are found to belong to a statistically different distribution using instant invention as shown in FIG. 3D. Moreover, making multiple target and reference measurements X' and X respectively enables instant invention to achieve far superior results. This is another major advantage of the invention over the prior art. For example, as taught herein, fitting measurements X' and X to distribution curves allows the instant invention to use a variety of statistical techniques for making mutation calls.

In a generalized variation of the above embodiment, a state is defined by k variables, and each variable is measured $n_k$ times. Let us assume that k=2, and the two variables are X and Y i.e. the state is defined as (X, Y). In the example below, let us further assume that $n_1=n_2=3$, yielding measurement groups X: $X_1, X_2, X_3$ and Y: $Y_1, Y_2, Y_3$. A profile array of X, Y measurements is shown in Table 2A. A second state (X', Y') is defined by a new set of measurements $X'_{1-3}$ and $Y'_{1-3}$. A profile array of X', Y' measurements is shown in Table 2B.

TABLE 2B

| index | | Quantity Measurements | | |
|---|---|---|---|---|
| i = | Variable | M1 | M2 | M3 |
| 1 | X' | $X'_1$ | $X'_2$ | $X'_3$ |
| 2 | Y' | $Y'_1$ | $Y'_2$ | $X'_3$ |

TABLE 2A

| index | | Quantity Measurements | | |
|---|---|---|---|---|
| i = | Variable | M1 | M2 | M3 |
| 1 | X | $X_1$ | $X_2$ | $X_3$ |
| 2 | Y | $Y_1$ | $Y_2$ | $X_3$ |

For each variable X: $X_1, X_2, X_3$ and Y: $Y_1, Y_2, Y_3$, we then calculate the probability that both states (X, Y) and (X', Y') belong to distributions having the same mean. As an example, using the above provided teachings of a statistical t-test, if p-value $\geq \alpha$ under the null hypothesis that states (X, Y) and (X', Y') belong to distributions having the same mean, then the two sets of measurements are not statistically different.

Otherwise, if p-value $<\alpha$, then states (X, Y) and (X', Y') are statistically different, and state variables X, Y are assembled in a differential (allelic) profile according to the above teachings. This generalized variation may be useful for comparing differences (mutations) between general physical variables of measurements. Note, that as already mentioned, that depending on the distributions (X, Y) and (X', Y'), other forms of t-tests may also be used for their comparison. For example, the Welch's test may be used when distributions (X, Y) and (X', Y') have unequal variances.

In still other advantageous embodiments, other distributions are used to fit the observed data for statistical comparison. The statistical comparison/test yields the statistical measure of significance between the sample and reference measurements. In a specific embodiment, the distribution used is a negative binomial distribution. Let us look at this embodiment employing a negative binomial distribution in more detail.

First, each possible base, for each sample and reference replicate, at each nucleotide/base position assayed is identified by an allele index i. Another way of saying this is that each possible allele, for each sample and reference replicate, at each nucleotide/base position or locus is identified by the allele index i. The reader may refer to Table 1 and the associated explanation of the relationship between allele index i and the corresponding measurement values for each possible base (A, T, G, or C) or allele at index i. In this explanation, we sometimes use the terms bases or alleles interchangeably, because it is at the level of the base or base-pairs that we are detecting mutations in the allele/gene.

Corresponding to each allele index i are any of a number of values representing the strength of the observation (after alignment and quality filtering) or the signal value, for the allele/base at index i. This signal value is an integer, or converted into an integer form. Exemplary types of signal values include a statistical average of the number of reads (or the count number) of a base at index i. The signal value may also be a digitized allele frequency AF value expressed as ((total number of reads of a base at an index i/total read-depth (or depth of coverage) at index i)*10,000.

Alternatively, the signal value may be the AF value scaled by a statistical average of the count number at index i, or it may be scaled by some other scalar/constant. The signal value may also be a normalized/standardized count number at index i computed, for example, as the mean of "standard scores" of the individual count numbers at index i. The statistical average in the various types of signal values above, may be the mean, median, mode, range, etc. and it may span one reference or target replicate where the read originated, or it may span the entire reference or target sample.

The choice of a given type of signal value above may be made based on the requirements of an implementation. Note that one would need to pick the same type of signal value to represent both the reference and sample measurements in the following computations. Now the signal value, or simply the signal, for the reference and sample is fit to a negative binomial distribution. The objective is to calculate a p-value describing the probability that a mutation exists in the target sample. The p-value, or a corresponding multiple hypothesis-adjusted p-value, forms the basis for mutation identification.

By multiple hypothesis-adjusted p-value we mean that the p-value is chosen over multiple (usually thousands of) potential mutation calls. For example, consider an amplicon panel with 40 kbp. Since each base-pair may be one of four bases, the total number of hypotheses tested is 4 (possible bases)×40,000 (bp)=160,000. As such, the cut-off $\alpha$ for the p-value chosen is across all potential 160,000 calls, rather than at just one allele index i. As such, the cut-off $\alpha$ is a lot more stringent for larger panels to preserve specificity.

Let us now mathematically demonstrate the current approach of fitting a reference signal A and a target signal B to a negative binomial distribution more rigorously. Let us assume that $m_A$ represents the number of reference replicates and $m_B$ represents the number of sample replicates. At each allele index position i, let us further denote the signal value of the reference by $q_{iA}$. See above explanation for the various possible types of signal values. Similarly, let us denote the signal value of the target by $q_{iB}$, assuming reference and target signal values are of the same type.

Let a null hypothesis stipulate that $q_{iA}=q_{iB}$ for all i. In other words, if the p-value $P_i$ at index i as determined below, follows: $P_i \geq$ cutoff/threshold $\alpha$, then the null hypothesis is true and there is no mutation in B compared to A. Moreover, if the null hypothesis is false, i.e. $P_i < \alpha$, then a mutation call is made at index i.

Furthermore, let us define:

$$Pr(K_{iA}=a) \qquad \text{Eq. 3,}$$

$$Pr(K_{iB}=b) \qquad \text{Eq. 4,}$$

where $K_{iA}$ represents the total of all count numbers at an allelic index i observed in the reference across all reference replicates. In the example of Table 1 above, at i=3, $K_{iA}=X_{31}+X_{32}+X_{33}$. Similarly, $K_{iB}$ represents the total of all count numbers at an allelic index i observed in the target across all target replicates. These two values are represented by a and b and the probabilities of these events occurring are expressed in Eq. 3 and Eq. 4 respectively. Because events a and b are independent under our null hypothesis, the probability of observing both events a and b as a pair, P(a,b) is given by:

$$P(a,b)=Pr(K_{iA}=a) \cdot Pr(K_{iB}=b).$$

Let us designate $K_{iS}=K_{iA}+K_{iB}$, representing the total count number at allelic index i across all reference and all target replicates. Then according to the present embodiment, the p-value $P_i$ that may be used to accept or reject the null hypothesis is given by the following equation:

$$P_i = \frac{\sum_{\substack{a+b=K_{iS} \\ p(a,b) \leq p(K_{iA}, K_{iB})}} p(a,b)}{\sum_{a+b=K_{iS}} p(a,b)} \qquad \text{Eq. 5}$$

In other words, p-value $P_i$ used to call a mutation in the sample at allele index i, is calculated by dividing two values. The numerator value is the sum of each computed probability of all events a and b in all the reference and sample replicates combined such that: (i) their total count $a+b=K_{iS}$ and (ii) the computed probability p(a,b) is less than or equal to the probability $p(K_{iA},K_{iB})$ of observing the actual count numbers $K_{iA}$ and $K_{iB}$. The denominator is the sum of each computed probability of all events a and b in all the reference and sample replicates combined such that their total count $a+b=K_{iS}$.

For a more in-depth review of the above approach employing negative binomial distribution in the context of gene expression analysis, the reader is referred to the NPL references, "Differential expression analysis for sequence count data", by Anders et al., dated November 2010 and appearing in Genome Biology 2010, 11:R106 and "Regression analysis of count data", by Cameron et al., 1998/2013 editions.

In variations of the above embodiment, it is envisioned that other distributions can be substituted for fitting measurement data besides the negative binomial distribution. For example, Poisson distribution would be a straightforward adaptation of the above teachings as will be appreciated with a person of ordinary skill. A person of ordinary skill will recognize that the Poisson distribution can be derived as a limiting case of the negative binomial distribution.

Specifically, if in a negative binomial distribution, as r (stopping parameter)$\to \infty$ and as p (probability of success in each trial)$\to 1$ and if $\mu$ (mean) stays constant, then $P(X=x)$ converges to $e^{-\mu}\mu^x/x!$, where X is a negative binomial random number, and P gives the density for a Poisson ($\mu$) distribution.

Other exemplary statistical distributions for fitting include normal or Gaussian distribution, Geometric distribution, Hypergeometric distribution, Discrete Uniform distribution, Gamma-Poisson mixture distribution, Binomial distribution, Beta distribution, Gamma distribution, etc. Furthermore, one can envision the use of other statistical tests known in the art to determine a measure of statistical significance of comparison between sample and reference measurements according to the present invention.

The superior performance of the present techniques and their comparison with various low frequency AF detection methods introduced in the background section, is shown in Table 3. Note the higher sensitivity and/or lower FP rate of the present invention at a given AF as compared to both background subtraction methods and molecular barcoding techniques of the traditional art. As taught herein, the present invention achieves these results by employing a number of different measurements of the sample by replicate sequencing, and statistically comparing these measurements against replicate reference measurements.

TABLE 3

| Technique | Panel/ Sequencing technology | Allele Frequency Range | Sensitivity | FP/10 kb | Mean Coverage | Panel Size Assayed |
| --- | --- | --- | --- | --- | --- | --- |
| Present Invention | Swift56G/ MiniSeq | 0.3-1% | 100% | 0 | 40000 | 44000 bp |
| Present Invention | GeneReadV2/ NextSeq | 0.5-1% | 91% | 0 | 38553 | 39603 bp |
| Present Invention | GeneReadV2/ NextSeq | 1-2% | 100% | 0 | 34642 | 39603 bp |
| Present Invention | TST15/ MiSeq | 0.3-1% | 100% | 0 | 40000 | 30531 bp |
| Lofreq | GeneReadV2/ NextSeq | 0.5-1% | 83% | 29.8 | 10000 | 39603 bp |
| Molecular Barcoding (Peng et al.) | Qiagen custom panel | 1-2% | 85% | 0.76 | 17365 | 39231 bp |
| Molecular Barcoding (Hiatt et al.) | Lab developed custom panel | 0.75-1.5% | 72% | 0.56 | 7076 | 125000 bp |
| Traditional caller (Frampton et al.) | Foundation Med Panel | 2-5% | 98% | 0.25 | >700x | |

In the preferred embodiments of the invention, 3-4 sample replicates and 3-4 reference replicates are employed. An illustration of such an experimental setup 300 is shown in FIG. 4. In the embodiment shown in FIG. 4, a reference DNA sample 302 is replicated, either technically or biologically into four corresponding reference replicates 308A, 308B, 308C and 308D. Similarly, a target/sample DNA 304 is replicated, either technically or biologically, into four corresponding target/sample replicates 310A, 310B, 310C and 310D.

The four reference replicates 308A-D and the four target replicates 310A-D are then sequenced in step 312 and 314 respectively. DNA sequencing steps 312, 314 may use an NGS sequencer and associated techniques, such as Illumina or Ion Torrent, etc. Steps 312 and 314 further consist of sub-step 1 of obtaining the raw sequencing data from a suitable sequencer, such as the one of those mentioned above. Then a sub-step 2 aligns the raw sequencing data from the reference replicates 308A-D and target replicates 310A-D to a human genome.

Sub-step 3 of steps 312, 314 is then used to perform the requisite quality scoring and filtering related to the alignment process known in the art. Sub-steps 1-3 are well understood in the art and will not be explained further in this disclosure. Also refer to the background section for explanation of quality scoring and read alignment.

Sub-steps 1, 2, and 3 of steps 312, 314 are precursors to the step of data analysis of sequencing data according to the invention. The result of DNA sequencing steps 312 and 314, and consequently the result of sub-steps 1-3 of steps 312 and 314 respectively, is the generation and collection of aligned and quality scored/filtered sequencing data. This data includes aligned and quality scored/filtered reference sequencing data, or simply reference sequence data, from reference replicates 308A-D as well as aligned and quality scored/filtered target sequencing data, or simply target sequencing data, from target replicates 310A-D.

Now a data processing and analysis step 316 is carried on the reference and target sequencing data obtained above. Step 316 may be a single step as shown in FIG. 4 or it may comprise a number of individual steps, each carrying out various functionalities encapsulated in step 316 of FIG. 4. Note, that other steps may also be carried out on target or sample replicates 308A-D and/or reference replicates 310A-D in system 300 but are not explicitly shown in FIG. 4. These preparatory operations/steps will be known to a person of average skill, and include amplification, lysing, isolation/sequestration, DNA extraction, preferential DNA capture, molecular barcoding, purification and enrichment of the genetic materials of the sample and/or the reference.

Of course, the various steps chosen to be performed on target/sample replicates 308A-D may be different and independent of the steps performed on reference replicates 310A-D. FIG. 4 further shows the reagents in vial 306, that may be needed to carry out one or more of the above steps, and specific to the amplicon panel being used. Note further that sub-steps 1-3 of data sequencing steps 312 and 314 may be combined with the data analysis step 316 if needed.

As shown in FIG. 4, data processing and analysis step 316, is further composed of sub-steps 4, 5, 6. In sub-step 4, a table or profile array consisting of the read counts at each possible locus for each target and reference replicate is created (see Table 1 and the associated explanation above). According to one embodiment, in sub-step 5, a p-value for the observed differences between the sample and reference replicates is computed using a negative binomial test. Subsequently, in sub-step 6, variants are called where multiple hypothesis testing of the negative binomial test yields a p-value <0.01 with an AF >0.4%.

FIG. 5 depicts a block diagram view of an exemplary architecture of a bioinformatics system 350 needed to perform the mutant/variant detection techniques according to the invention. Specifically, in bioinformatics system 350, external inputs of a set of reference replicates 352 and a set of target replicates 354 are sequenced by a sequencing module 356. Sequencing module 356 may be an industrially available Next Generation Sequencing (NGS) module, such as, Illumina, Ion Torrent, etc.

Raw reads from NGS module 356, in the form of fastq files is provided to a data processing module 360. Data processing module 362 in turn consists of a number of other modules. Specifically, an alignment and quality scoring/filtering module 362 aligns the reads to a standard human genome. Standard human genome data 358 is available as an input to module 362, using which it performs its alignment, scoring and filtering functions.

Aligned and filtered reference and target sequencing data from module 362 is then populated into the one or more allelic profile arrays 374. This function is preferably performed in two steps. Specifically, a profile creation module 364 first creates one or more profile arrays 374 and a profile array population module 366 then populates profile array(s) 374 with the aligned and filtered sequencing data obtained from module 362 above. As shown in FIG. 5, a bioinformatics database 372 may be used to store the allelic profile array(s) 374 populated with the aligned and filtered reference and target sequencing data, or reference and target sequencing data for short. Note that many variations of this design employing multiple databases or various types of databases are conceivable for those skilled in the art.

A data analysis module 368 with access to the reference and target sequencing data stored in database 372 is responsible for analyzing the data per above teachings. Specifically, data analysis module may analyze the data according to a Student's t-test (see Eq. 1-2 and the associated teachings), or it may fit the data to a negative binomial distribution (see Tables 1, 2A-B and Eqs. 3-5 and the associated teachings), or it may fit the data to some other type of distribution (e.g. Poisson, Geometric, etc.), or it may still analyze the data according to some other appropriate statistical test.

Based on the analysis performed by data analysis module 368, a variant calling and reporting module 370 is invoked to make calls on the variants found in target sample replicates 354. The calls made by reporting module 370 can then again be stored into database 272 for any desired subsequent processing/analysis. The calls reported by module 370 may be in one or more files in a suitable file format, such as, variant call format (vcf) file(s) indicated in FIG. 5.

Indeed, various alternative computational architectural designs are possible within the scope of the invention to practice the teachings provided herein. Such system designs will be familiar to those skilled in the art of bioinformatics systems design. As such the embodiments described in relation to FIG. 5 are exemplary to explain the features and functions of the invention, with the admission of other alternative designs possible for those familiar with the art.

A variation of the present embodiment compares the target sample replicates against a predetermined background of reference sample replicates that is provided based on prior experiments. In this variation, an a priori reference background dataset already exists that was established based on reference replicates as taught herein. Then multiple target samples are analyzed/compared against the same reference background using the current teachings. Of course, each such target sample would be replicated into its corresponding target replicates prior to sequencing and analysis, also as per current teachings. This variation has the advantage of greatly reducing the amount of sequencing required for each target sample tested. This is because the same reference background is reused for the statistical analysis and mutation detection of several target samples.

Alternatively, one can also employ a set of target sample replicates compared to a single a background reference sample, as well as a single target sample compared to a set of several background or reference replicates. Let us now look at a concrete example of applying the teachings of the instant invention to demonstrate the increased ability to detect low frequency alleles in a DNA mixture. As explained, the example below employs multiple reference and target replicates according to the advantageous embodiments taught herein.

Example 2

1. Introduction

In our example, the DNA mixture consists of the targeted amplicon panel Qiagen GeneRead v2 which is a clinically relevant tumor panel. Targeted amplicon panels are commonly employed to assess genomic regions of interest for clinically relevant mutations in a patient's DNA. In the case of cancer diagnosis and monitoring, the mutations detected have implications for treatment regimens and prognosis. The patient DNA sample comes in the form of a mixture of alleles representing DNA originating from cells of diverse origins.

The diverse alleles in the mixture may represent heterogeneity in the cancer-derived cell population as well as contamination from non-cancer tissue. Consequently, some alleles of clinical interest may be present in the DNA sample below the limit of detection of the test. This problem may occur in solid tumor biopsies in the case where a clinically relevant subclonal tumor cell population is present below the limit of detection. Furthermore, this limit of detection problem is pervasive in mutation detection from blood biopsies where contamination from wild-type DNA is relatively high. Alleles of this class are often in the sub 1% AF frequency range and are not detectable by techniques of the prior art.

To mimic the above scenario, we prepared a DNA sample containing various mutations (mutations present in tumor cell line derived DNA) at a concentration of between 0.5-1% AF in a wild-type background and used the present invention to identify them. We employed the above techniques using the Qiagen GeneReadv2 Clinically Relevant Tumor Panel and demonstrated the superiority of the present invention with respect to the state of the art by providing better performance than the reagent manufacturer.

2. DNA Samples

The DNA samples used were acquired from Coriell Institute for Medical Research. The DNA samples acquired were from two different cell lines, NA12878 and NA19129. These DNA samples represent two human individuals of distinct ancestry and thus provide ample polymorphisms for testing detection capabilities. From these two pure cell line DNA samples, three test samples were prepared for sequencing. Sample 1 was pure NA19129 DNA, sample 2 was pure NA12878 DNA, and Sample 3 was a mixture of 1 part NA12878 DNA to 99 parts NA19129 DNA.

Sample 1 was used as the reference and provided material for the reference replicates, sample 2 provided an empirical standard for the mutations present in NA12878 with respect to NA19129, and sample 3 was used as the target and provided a challenging admixture with NA12878 heterozygous alleles at 0.5% AF and homozygous alleles at 1% AF.

3. Library Preparation and Next-Generation Sequencing

The Qiagen GeneReadv2 Clinically Relevant Tumor Panel was used according to manufacturer's instructions for targeted amplicon library preparation. Four libraries were made from the reference (sample 1), one library was made from sample 2, and four libraries were made from the target (sample 3). Libraries were multiplexed and sequenced on Illumina Next-Seq at approximately 10,000× coverage.

4. Data Analysis

Sequencing data was demultiplexed into fastq files corresponding to each library. Primer sequences were trimmed from all fastq files and fastq files were then aligned to the human genome (hg19) using BWA mem. A standard caller was used to filter alignment files for base quality and mapping quality and to produce an output of all base calls.

Sample 1 (reference) and sample 2 (empirical standard) vcfs were compared to identify germ line differences between NA19129 and NA12878. 11 germ line differences across the amplicon panel were discovered between NA19129 and NA12878. These 11 differences were expected to be present between 0.5% and 1% AF in sample 3 and are indicative of the performance of the present invention.

Custom software was used to create a single allele profile array containing both reference and target measurements per above teachings. Measurements from the four reference replicates (from sample 1) and the four target replicates (from sample 3) respectively were populated into the profile array. Per earlier teachings, measurements corresponding to each allele index value across the panel consisted of four digitized AF values from the reference replicates (sample 1) and four digitized AF values from the sample replicates (sample 3).

The digitized allele frequencies AF values were expressed in percentage and computed as: (total number of mutant index base calls at index i/total depth of coverage at index i) * 10'000. The allele profile array was then analyzed using a negative binomial test as described above in order to calculate a p-value $P_i$ from Eq. 5. p-value $P_i$ expressed the differential presence of an allele at each index between sample and reference replicates. Custom software was then used to identify allele indices showing mutation/enrichment in the sample with a multiple hypothesis-adjusted p-value lower than 0.01.

5. Results

The present invention showed remarkable improvements over traditional variant calling workflows in its ability to detect the mutations in sample 3. The improvements were evidenced by gains in both sensitivity and specificity when compared against the same standard caller for a single replicate run. The standard caller used in this example Lofreq has been shown to perform well with respect to other variant calling algorithms. Specifically, Lofreq was able to detect 83% of mutations while calling 118 false positives. In a stark contrast however, the present invention was able to detect 91% of mutations with zero false positives (FP)!

In Table 3, the corresponding rows showing the above measurements for the present invention, termed as ERASE, and Lofreq traditional caller are underlined. These outstanding gains over the prior art are also shown in the comparison chart 400 of FIG. 6. The chart shows measurements 402 by hollow circles for the target (sample 3) using the Qiagen GeneRead V2 panel in the example described above. In contrast, the measurements 406 using traditional variant calling software Lofreq of the prior art are shown by crosses. Specifically, FIG. 6 shows data resulting from the application of the invention to sequence data generated from DNA mixtures containing low AF variants (0.1-1%). Here the number of false positives are reported as a function of the AF cutoff employed.

Note that the false positive rate increases dramatically when using standard variant caller of the traditional art, that employ base quality alone as a filter. As shown by measurements 406 with the standard techniques of the art, the false positive (FP) rate increases from about 1 FP/kb at 0.5% AF to about 20 FPs/kb close to 0.1% AF. Note also that the full panel is about 40 kb in size. Below a threshold of 0.5% AF (0.005 fraction), the false positive report rate for standard NGS techniques starts increasing quickly, reaching about 5 false calls per kb sequenced at 0.3% AF.

In contrast, using the instant techniques, the FP calls are dramatically reduced to 0 FPs/kb at 0.2% AF and about 1 FP/kb at 0.1% AF as shown by measurements 402 in FIG. 6. Employing 4 sample replicates compared to 4 reference replicates according to the present example (also see the embodiment of FIG. 4 and the associated explanation), eliminates all false positives at the same cutoff of 0.3% AF, and a majority of FPs at lower cutoffs. Further note that the sensitivity of the instant approach remains very high, with all spikes in variants being detected all the way down to 0.2% AF.

Importantly, the current approach is orthogonal with other approaches that have been shown to reduce error rates and to improve sensitivity. For example, single molecule barcoding methods may be used for each of the replicates that are being run to further reduce error rates. See NPL references Lanman et al., Peng et al. and Hiatt et al. introduced in the background section. One interesting way to combine these approaches is to use barcoding followed by the comparison of one or more sample replicates with one or more reference replicates in accordance with the teachings provided herein. In a similar variation, the above comparison could employ a background error level based on the references.

Other combinations of the sequencing error reductions and sensitivity improvement methods presented in the background section and the present techniques will be apparent to a person of average skill. The combination of these techniques will lead to even lower error rates at higher sensitivities as the effects of the methods are likely to be cumulative.

As will be clear by now, that a system for applying the invention would include a set of abnormality/mutation AF measurements (or calls) for multiple replicates of the same target sample. It would further include a set of abnormality/mutation AF measurements from multiple reference replicates, and an algorithm comparing the two sets of AF measurements to determine which target sample calls were present in the starting sample (as opposed to being generated by process errors). Such a system enables the determination of starting sample abnormalities with very high sensitivity and specificity and can be applied to a number of problem areas such as somatic mutation detection in liquid biopsy samples, somatic mutation detection in solid biopsy samples, determination of fetal abnormalities, transplant rejection, or pathogen detection.

Tests or assays employing the instant invention are envisioned for a variety of diagnostic and translational uses within key therapeutic areas. In the area of cancer diagnosis, these approaches might be used to diagnose the presence of tumor material at low AF % ages while using liquid biopsies or solid biopsies with low tumor content. Subjects may be tested from the general population for screening purposes, or from a population with elevated risk factors for cancer, e.g. hereditary, lifestyle or symptomatic factors.

In the area of cancer treatment, the liquid biopsy testing taught herein may be used in lieu of a solid tumor biopsy, to monitor the response to therapy over time or for the emergence of resistance, or to prescribe the best treatment. The same type of measurements may be performed in a translational setting, for patients participating in clinical trials. The invention may be used to determine the presence of somatic mutations and other abnormalities with higher accuracy as compared to existing methods, or in samples with insufficient tumor materials for evaluation with standard methods. In the area of non-invasive pre-natal diagnosis (NIPT) the inventions described may be used to determine the presence of genetic fetal abnormalities by using a blood sample from the expectant mother. In the area of pathogen detection of viral diagnostics, the invention may be used to determine mutations occurring in small viral or bacterial sub-populations.

In order to enable the application of the invention at a number of different sites, a testing and analysis kit can also be provided. Such a kit would comprise a set of reagents needed to perform the sample preparation before sequencing, and a set of instructions or computer code capable of performing the algorithms described. The code may be provided on a storage medium such as a disk drive, USB drive, Secure Digital (SD) card, etc.

Alternatively, the code may be made available in the cloud with instructions on how to upload the experimental data to a cloud based (web) application and receive the resulting variants. The kit may also include targeted amplification chemistries with locus/position-specific background error rates for various targeted panels. The kit may also include locus/position-specific reference sequencing data as applied to one or more of the above taught statistical techniques/tests.

For example, the kit may include reference sequencing data in reference profile array(s) that is ready to be applied to a Student's t-test, or fit to a negative binomial distribution or fit to a Poisson distribution according to the above teachings. Background/reference error rates specific to popular sequencer equipment and associated processes may also be provided. Such a kit with a background error model, or reference sequencing data, along with the specific sequencing reagents will allow the instant invention to be practiced in a variety of commercial and lab settings.

Such a system may also include reagents for one or more of the following operations: cell isolation, cell lysis, nucleic acid extraction and purification, DNA capture, liquid sample storage, shipping/transport and processing, reagents for the preferential capture of mutant sequences and reagents needed for targeted amplification of multiple samples/replicates sub-divided from the same starting sample. The kit may include reagents and consumables for circulating tumor cell enrichment from blood or other bodily fluids and/or reagents for free DNA extraction from blood, urine, or other bodily fluids. Furthermore, the system may also include reagents and consumables for exosome extraction from blood, urine, or other bodily fluids. As already mentioned, the system may include reagents and consumables for the extraction, storage and transport of biopsy samples.

It should be noted that the teachings of this disclosure apply equally to detecting alterations in any nucleic acid sequence, including a DNA or an RNA sequence. For ease of explanation however, the embodiments above may employ DNA samples. But nonetheless, the reader is instructed to understand that the mutation detection techniques taught herein apply to such detection in any nucleic acid sequence whose target and reference replicates are being analyzed and compared according to the current teachings.

In view of the above teaching, a person skilled in the art will recognize that the teachings and methods of present invention can be embodied in many different ways in addition to those described without departing from the principles of the invention. Therefore, the scope of the invention should be judged in view of the appended claims and their legal equivalents.

We claim:

1. A method of detecting at least one genetic alteration in a target sample, said method comprising the steps of:
    (a) obtaining a plurality of target replicates from said target sample;
    (b) obtaining a plurality of reference replicates from a reference sample;
    (c) obtaining target sequencing data from said target replicates and reference sequencing data from said reference replicates; and
    (d) detecting said at least one genetic alteration by comparing said target sequencing data and said reference sequencing data in accordance with a statistical test, said statistical test performed by program instructions stored in a non-transitory computer-readable storage medium.

2. The method of claim 1, where said target sample and said reference sample are derived from an item selected from the group consisting of a single donor and different donors.

3. The method of claim 1, where said statistical test applies said target sequencing data and said reference sequencing data to an item selected from the group consisting of a Student's t-test, a negative binomial distribution and a Poisson distribution.

4. The method of claim 3, further computing a p-value to indicate a probability that said at least one genetic alteration exists in said target sample.

5. The method of claim 4, further storing said target sequencing data and said reference sequencing data in one or more allelic profile arrays, said one or more allelic profile arrays comprising read values for said target replicates and said reference replicates, at each allelic index.

6. The method of claim 5, where said one or more allelic profile arrays are organized as one or more tables residing in a database.

7. The method of claim 1, further comparing a statistical average of a first set of measurements at a locus in said target replicates and said statistical average of a second set of measurements at said locus in said reference replicates, and performing said statistical test based on said comparison.

8. The method of claim 1, where based on said at least one genetic alteration further performing a step selected from the group consisting of diagnosing a cancer, diagnosing an auto-immune disease, detecting a probability of an organ transplant rejection, detecting a genetic fetal abnormality, detecting a pathogen and determining an efficacy of a cancer treatment.

9. The method of claim 8, where said step is detecting a pathogen, and further detecting one or more mutations occurring in an item selected from the group consisting of a viral sub-population and a bacterial sub-population.

10. A system comprising:
    (a) a plurality of target replicates derived from a target sample, said target sample containing one or more genetic alterations;
    (b) a plurality of reference replicates derived from a reference sample; and
    (c) target sequencing data obtained from said target replicates and reference sequencing data obtained from said reference replicates, said target sequencing data and said reference sequencing data stored in a non-transitory computer-readable storage medium;
    wherein said one or genetic alterations are detected based on comparing said target sequencing data and said reference sequencing data in accordance with a statistical test.

11. The system of claim 10, wherein said statistical test is based on applying said target sequencing data and said reference sequencing data to an item selected from the group consisting of a Student's t-test, a negative binomial distribution and a Poisson distribution.

12. The system of claim 10, further comprising a capability for at least one item selected from the group consisting of diagnosing a cancer, diagnosing an auto-immune disease, computing a probability of an organ transplant rejection, diagnosing a genetic fetal abnormality, detecting a pathogen mutation and determining an efficacy of a cancer treatment.

13. The system of claim 10, further utilizing one or more molecular barcodes in said item (c) for said obtaining of said target sequencing data and said reference sequencing data.

14. The system of claim 10, further comprising a testing and analysis kit, said kit comprising reagents for performing a preparatory operation on at least one item selected from the group consisting of said plurality of target replicates and said plurality of reference replicates.

15. The system of claim 14, wherein said kit further comprises computer instructions for implementing said statistical test, said computer instructions stored in a non-transitory computer-readable storage medium.

16. The system of claim 15, wherein said non-transitory computer-readable storage medium resides in a computer cloud.

17. The system of claim 15, wherein said kit further comprises targeted amplification chemistries of one or more targeted panels.

18. The system of claim 15, wherein said kit further comprises background error rates specific to popular sequencer equipment and processes.

19. The system of claim 10, wherein said target sequencing data and said reference sequencing data is stored in one or more allelic profile arrays.

* * * * *